United States Patent
Kim et al.

(10) Patent No.: US 12,240,803 B2
(45) Date of Patent: Mar. 4, 2025

(54) DIAMINE COMPOUND, AND POLYIMIDE PRECURSOR AND POLYIMIDE FILM USING SAME

(71) Applicant: LG CHEM, LTD., Seoul (KR)

(72) Inventors: Jeeseon Kim, Daejeon (KR); Kyunghwan Kim, Daejeon (KR); Hoyong Lee, Daejeon (KR); Cheol Jun Song, Daejeon (KR)

(73) Assignee: LG CHEM, LTD., Seoul (KR)

( * ) Notice: Subject to any disclaimer, the term of this patent is extended or adjusted under 35 U.S.C. 154(b) by 822 days.

(21) Appl. No.: 17/312,629

(22) PCT Filed: Feb. 14, 2020

(86) PCT No.: PCT/KR2020/002138
§ 371 (c)(1),
(2) Date: Jun. 10, 2021

(87) PCT Pub. No.: WO2020/175838
PCT Pub. Date: Sep. 3, 2020

(65) Prior Publication Data
US 2022/0017461 A1  Jan. 20, 2022

(30) Foreign Application Priority Data

Feb. 28, 2019 (KR) .................. 10-2019-0023818
Jan. 16, 2020 (KR) .................. 10-2020-0006133

(51) Int. Cl.
*C07C 323/42* (2006.01)
*C08G 73/10* (2006.01)
*C08J 5/18* (2006.01)

(52) U.S. Cl.
CPC ............ *C07C 323/42* (2013.01); *C08G 73/10* (2013.01); *C08J 5/18* (2013.01); *C08J 2379/08* (2013.01)

(58) Field of Classification Search
CPC .................... C07C 323/42; C08G 73/1064
See application file for complete search history.

(56) References Cited

U.S. PATENT DOCUMENTS 5,130,481 A * 7/1992 Khanna ................ C07C 317/40
564/154

FOREIGN PATENT DOCUMENTS

| CN | 1146463 A | * | 4/1997 |
| JP | 2016-117688 A | | 6/2016 |
| KR | 10-2015-0141029 A | | 12/2015 |
| KR | 10-2017-0092925 A | | 8/2017 |
| KR | 10-2018-0104490 A | | 9/2018 |

OTHER PUBLICATIONS

CAS Abstract and Indexed Compound S. Kumar, et al., 27 Journal of medicinal chemistry 1083-1089 (1984) (Year: 1984).*
International Search Report issued for International Application No. PCT/KR2020/002138 on Jun. 16, 2020, 4 pages.
Waris et al., "Synthesis and characterization of processable aromatic polyimides and their initial evaluation as promising biomaterials", Colloid Polym Sci., 2013, vol. 291, 1581-1593.
Kil et al., "Preparation and Thermal Properties of Enaryloxynitriles End-Capped polymer Precursors", Bulletin of the Korean Chemical Society. 2000, vol. 21, No. 6, 557-561.
Sadeghpour et al., "2,2'-Thio-bis[(4-methylphenyl)-2-aminobenzoate]", Molbank, 2012, M760; doi:10.3390/M760.
Huang et al., "Synthesis and characterization of thioether-containing polyimides with high refractive indices", J. Polym. Res., 2012, 19:9790.
Kumar et al., "Syntheses and Anthelmintic Activity of Alkyl 5(6)-(Substituted-carbamoyl)-and 5(6)-(Disubstituted-carbamoyl)benzimidazole-2-carbamates and Related Compounds", J. Med. Chem., 1984, 27, 1083-1089.
Avotinsh et al, "Reactions of Isatoic Anhydride With Diamines", Materials Sciences and Applied Chemistry 2008, vol. 16, No. 1, pp. 142-147.
Zhou et al., "An oxidation-induced fluorescence turn-on approach for non-luminescent flexible polyimide films", Journal of Materials Chemistry C, 2017, 5, 8545-8552.

* cited by examiner

*Primary Examiner* — Alexander R Pagano
*Assistant Examiner* — Frank S. Hou
(74) *Attorney, Agent, or Firm* — ROTHWELL, FIGG, ERNST & MANBECK, P.C.

(57) ABSTRACT

Disclosed is a novel diamine compound comprising a structure in which diphenyl sulfide in a molecule is bonded through an amide bond to a phenyl ring substituted with an amine group. A polyimide film prepared by polymerizing the novel diamine compound exhibits improved mechanical and thermal properties and an enhanced refractive index.

4 Claims, No Drawings

DIAMINE COMPOUND, AND POLYIMIDE PRECURSOR AND POLYIMIDE FILM USING SAME

CROSS-REFERENCE TO RELATED APPLICATION

This application a 35 U.S.C. 371 National Phase Entry Application from PCT/KR2020/002138, filed on Feb. 14, 2020 and designating the United States, which claims the benefit of priorities to Korean Patent Application Nos. 10-2019-0023818, filed on Feb. 28, 2019 and 10-2020-0006133, filed on Jan. 16, 2020, the entire disclosures of which are incorporated herein by reference.

FIELD OF THE INVENTION

The present invention relates to a novel diamine and a polyimide precursor and a polyimide film by using the same.

BACKGROUND OF THE INVENTION

In recent years, weight reduction and miniaturization of products have been emphasized in the field of display. A currently used glass substrate is heavy and brittle and is difficult to apply to a continuous process. Accordingly, researches are actively carried out for applying a plastic substrate having advantages of lightness, flexibility, and applicability to continuous process and substitutable for a glass substrate, to a cell phone, a notebook and a PDA (personal digital assistant).

Polyimide has heat resistance and chemical resistance, and especially aromatic polyimide exhibits excellent characteristics such as excellent mechanical properties and electrical insulation due to its rigid main chain structure. In addition, since the polyimide is easy to be synthesized, can be formed into a thin film and does not require a crosslinking agent for curing, it is widely used as a material for integration in semiconductor such as automotive and aerospace materials, liquid crystal displays (LCDs), and plasma display panels (PDPs), as well as daily supplies. Moreover, many studies have progressed for polyimide to apply to a flexible plastic display board having light and flexible characteristics.

A polyimide film, which is produced by film-forming the polyimide, is generally prepared by solution polymerization of aromatic dianhydride and aromatic diamine or aromatic diisocyanate to prepare a solution of polyamic acid derivative, coating the solution on a silicon wafer or a glass, and curing by heat treatment.

A flexible device involving a high temperature process requires heat resistance at high temperatures. In particular, an organic light emitting diode (OLED) device manufactured using a low temperature polysilicon (LTPS) process may have a process temperature close to 500° C. However, at this temperature, thermal decomposition by hydrolysis tends to occur even with the polyimide having excellent heat resistance. Therefore, to manufacture a flexible device, it is necessary to develop a polyimide film which exhibits excellent thermal properties and storage stability so that thermal decomposition by hydrolysis during the high temperature process does not occur.

BRIEF SUMMARY OF THE INVENTION

The present invention provides a novel diamine compound for preparing a polyimide with improved thermal and mechanical properties and improved refractive index.

The present invention also provides a polyimide precursor prepared using the novel diamine compound.

Still the present invention provides a polyimide film prepared by using the polyimide precursor and a flexible device comprising the polyimide film.

There is provided a diamine compound of the following formula 1:

[Formula 1]

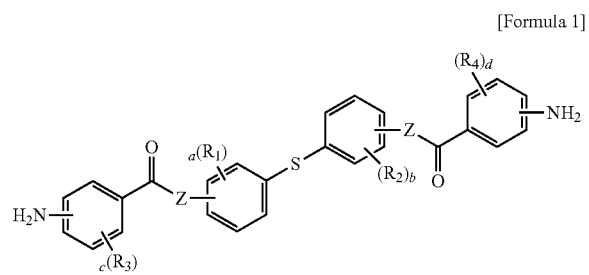

In the formula 1,

Z is —NH—, $R_1$ to $R_4$ are each independently hydrogen, deuterium, a halogen atom, a cyano group, a substituted or unsubstituted alkyl group having 1 to 30 carbon atoms, a substituted or unsubstituted haloalkyl group having 1 to 30 carbon atoms, a substituted or unsubstituted alkylsilyl group having 1 to 30 carbon atoms, a substituted or unsubstituted arylsilyl group having 6 to 30 carbon atoms, a substituted or unsubstituted alkylamino group having 1 to 30 carbon atoms, a substituted or unsubstituted arylamino group having 6 to 30 carbon atoms, a substituted or unsubstituted alkoxy group having 1 to 30 carbon atoms, a substituted or unsubstituted alkylthio group having 1 to 30 carbon atoms, a substituted or unsubstituted arylthiol group having 6 to 30 carbon atoms, a substituted or unsubstituted aryl group having 6 to 30 carbon atoms, a substituted or unsubstituted aralkyl group having 6 to 30 carbon atoms, a substituted or unsubstituted aryloxy group having 6 to 30 carbon atoms, a substituted or unsubstituted cycloalkyl group having 3 to 30 carbon atoms, an amide group, a substituted or unsubstituted cycloalkyloxy group having 3 to 30 carbon atoms, a substituted or unsubstituted cycloalkylthio group having 1 to 30 carbon atoms, an ester group, an azide group, a nitro group, or a substituted or unsubstituted (3-30 membered) heteroaryl group comprising at least one selected from B, N, O, S, P(=O), Si and P, and a, b, c and d are each an integer of 0 to 4, and when a, b, c and d are each an integer of 2 to 4, each of a, b, c and d may be the same or different.

Effect of the Invention

The diamine compound of the present invention is a novel compound comprising a structure in which diphenyl sulfide in the molecule is bonded to a phenyl ring substituted with an amine group via the amide bond, and the polyimide containing it as a polymerization component can provide a polyimide film having improved heat resistance and mechanical properties after curing and exhibiting improved refractive index.

DETAILED DESCRIPTION OF THE INVENTION

Since various modifications and variations can be made in the present invention, particular embodiments are illustrated in the drawings and will be described in detail in the detailed description. It should be understood, however, that the invention is not intended to be limited to the particular embodiments, but includes all modifications, equivalents, and alternatives falling within the spirit and scope of the invention. In the following description of the present invention, detailed description of known functions will be omitted if it is determined that it may obscure the gist of the present invention.

Aromatic polyimides are widely used in high-tech industries such as microelectronics, aerospace, insulating materials and refractory materials due to their excellent overall properties such as thermal oxidation stability, and high mechanical strength. However, aromatic polyimides having strong absorbance in ultraviolet-visible region exhibit coloration from pale yellow to dark brown. It limits their wide application in the optoelectronics area, where transparency and colorless properties are basically required. The reason for the coloration in the aromatic polyimide is that intramolecular charge transfer complexes (CT-complexes) are formed between an alternating electron donor (dianhydride) and an electron acceptor (diamine) in the polymer main chain.

To solve this problem, methods for introducing specific functional groups, bulky pendant groups, fluorinated functional groups, etc. into the polymer main chain, or introducing —S—, —O—, —CH$_2$—, etc. have been studied to development an optically transparent polyimide film having high glass transition temperature (Tg), The inventors of the present invention have made extensive studies to solve the problems of the prior art and discovered that a novel diamine compound having a specific structure provides excellent thermal and mechanical properties, and thus completed the present invention.

Accordingly, the present invention provides a diamine of the following formula 1:

[Formula 1]

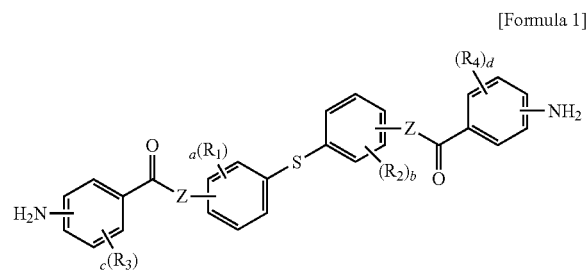

In the formula 1,

Z is —NH—,

R$_1$ to R$_4$ are each independently hydrogen, deuterium, a halogen atom, a cyano group, a substituted or unsubstituted alkyl group having 1 to 30 carbon atoms, a substituted or unsubstituted haloalkyl group having 1 to 30 carbon atoms, a substituted or unsubstituted alkylsilyl group having 1 to 30 carbon atoms, a substituted or unsubstituted arylsilyl group having 6 to 30 carbon atoms, a substituted or unsubstituted alkylamino group having 1 to 30 carbon atoms, a substituted or unsubstituted arylamino group having 6 to 30 carbon atoms, a substituted or unsubstituted alkoxy group having 1 to 30 carbon atoms, a substituted or unsubstituted alkylthio group having 1 to 30 carbon atoms, a substituted or unsubstituted arylthiol group having 6 to 30 carbon atoms, a substituted or unsubstituted aryl group having 6 to 30 carbon atoms, a substituted or unsubstituted aralkyl group having 6 to 30 carbon atoms, a substituted or unsubstituted aryloxy group having 6 to 30 carbon atoms, a substituted or unsubstituted cycloalkyl group having 3 to 30 carbon atoms, an amide group, a substituted or unsubstituted cycloalkyloxy group having 3 to 30 carbon atoms, a substituted or unsubstituted cycloalkylthio group having 1 to 30 carbon atoms, an ester group, an azide group, a nitro group, or a substituted or unsubstituted (3-30 membered) heteroaryl group comprising at least one selected from B, N, O, S, P(=O), Si and P, and a, b, c and d are each an integer of 0 to 4, and when a, b, c and d are each an integer of 2 to 4, each of a, b, c and d may be the same or different.

The term "substituted" in the description of "substituted or unsubstituted" as described herein means that a hydrogen atom in any functional group is replaced by another atom or another functional group, i.e., another substituent.

In the formula 1, substituents of the substituted alkyl group, the substituted haloalkyl group, the substituted alkylsilyl group, the substituted arylsilyl group, the substituted alkylamino group, the substituted arylamino group, the substituted alkoxy group, the substituted alkylthio group, the substituted arylthio group, the substituted aryl group, the substituted aralkyl group, the substituted aryloxy group, the substituted cycloalkyl group, the substituted cycloalkyloxy group, the substituted cycloalkylthio group and the substituted heteroaryl group are each independently at least one selected from the group consisting of deuterium, a halogen atom, a cyano group, an amino group, a carboxyl group, a nitro group, a hydroxy group, an alkyl group having 1 to 30 carbon atoms, an alkenyl group having 2 to 30 carbon atoms, an alkynyl group having 2 to 30 carbon atoms, an alkoxy group having 1 to 30 carbon atoms, an alkylthio group having 1 to 30 carbon atoms, an arylthio group having 6 to 30 carbon atoms, an aryl group having 6 to 30 carbon atoms, a cycloalkyl groups having 3 to 30 carbon atoms, a cycloalkenyl group having 3 to 30 carbon atoms, an aryloxy group having 6 to 30 carbon atoms, an alkylsilyl group having 1 to 30 carbon atoms, an arylsilyl group having 6 to 30 carbon atoms, an alkylamino group having 1 to 30 carbon atoms, an arylamino group having 6 to 30 carbon atoms, an alkylcarbonyl group having 1 to 30 carbon atoms, an alkoxycarbonyl group having 1 to 30 carbon atoms, an arylcarbonyl group having 6 to 30 carbon atoms, an alkylboronyl group having 1 to 30 carbon atoms, an arylboronyl group having 6 to 30 carbon atoms and (3-7 membered) heterocycloalkyl group.

As used herein, "alkyl having 1 to 30 carbon atoms" means straight-chain or branched alkyl having 1 to 30 carbon atoms, preferably 1 to 20 carbon atoms, and more preferably 1 to 10 carbon atoms. Specific examples of the alkyl include methyl, ethyl, n-propyl, isopropyl, n-butyl, isobutyl, tert-butyl, and the like.

As used herein, "alkenyl having 2 to 30 carbon atoms" means straight-chain or branched alkenyl having 2 to 30 carbon atoms, preferably 2 to 20 carbon atoms, and more preferably 2 to 10 carbon atoms. Specific examples of the alkenyl include vinyl, 1-propenyl, 2-propenyl, 1-butenyl, 2-butenyl, 3-butenyl, 2-methylbut-2-enyl, and the like.

As used herein, "alkynyl having 2 to 30 carbon atoms" means straight-chain or branched alkynyl having 2 to 30 carbon atoms, preferably 2 to 20 carbon atoms, and more preferably 2 to 10 carbon atoms. Examples of the alkynyl include ethynyl, 1-propynyl, 2-propynyl, 1-butynyl, 2-butynyl, 3-butynyl, 1-methylpenta-2-ynyl, and the like.

As used herein, "alkoxy having 1 to 30 carbon atoms" means straight-chain or branched alkoxy having 1 to 30 carbon atoms, preferably 1 to 20 carbon atoms, and more preferably 1 to 10 carbon atoms. Examples of the alkoxy include methoxy, ethoxy, propoxy, isopropoxy, 1-ethylpropoxy, and the like.

As used herein, "cycloalkyl having 3 to 30 carbon atoms" means a monocyclic or polycyclic hydrocarbon having 3 to 30 carbon atoms, preferably 3 to 20 carbon atoms, and more preferably 3 to 7 carbon atoms. Examples of the cycloalkyl include cyclopropyl, cyclobutyl, cyclopentyl, cyclohexyl, and the like.

As used herein, "aryl(ene) having 6 to 30 carbon atoms" means a monocyclic or fused cyclic radical derived from an aromatic hydrocarbon having 6 to 30 carbon atoms, preferably having 6 to 20 ring skeleton carbon atoms, and more preferably having 6 to 15 ring skeleton carbon atoms. Examples of the aryl include phenyl, biphenyl, terphenyl, naphthyl, fluorenyl, phenanthrenyl, anthracenyl, indenyl, triphenylenyl, pyrenyl, tetracenyl, perylenyl, chrysenyl, naphthacenyl, fluoranthenyl, and the like.

As used herein, "(3-30 membered) heteroaryl(ene)" means that an aryl(ene) group having 3 to 30 ring skeleton atoms and containing one or more selected from the group consisting of B, N, O, S, P(=O), Si and P. The heteroaryl group preferably has 3 to 20 ring skeleton carbon atoms, and more preferably 3 to 15 ring skeleton carbon atoms and preferably contains 1 to 4 heteroatoms. The heteroaryl group may be a monocyclic group or fused ring condensed with one or more benzene rings and may be partially saturated. In addition, the heteroaryl as used herein includes one or more heteroaryl groups or aryl groups connected to a heteroaryl group by a single bond. Examples of the heteroaryl include monocyclic heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl and pyridazinyl, and fused cyclic heteroaryl such as benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindoly, indolyl, indazolyl, benzothiadiazolyl, quinolyl, isoquinolyl, cynolinyl, quinazolinyl, quinoxalinyl, carbazolyl, phenoxazinyl, phenanthridinyl and benzodioxolyl.

As used herein "halogen" includes F, Cl, Br and I atoms.

As used herein, "(3-7 membered) heterocycloalkyl" means a cycloalkyl having 3 to 7 ring skeleton atoms and containing one or more heteroatom selected from the group consisting of B, N, O, S, P(=O), Si and P, preferably one or more heteroatoms selected from the group consisting of O, S and N, for example, pyrrolidine, oxathietane, tetrahydropyran, and the like.

According to an embodiment, in the compound of the formula 1, $R_1$ to $R_4$ are each independently hydrogen, a halogen atom, a cyano group, or an alkyl group having 1 to 6 carbon atoms which is unsubstituted or substituted with a halogen atom, and a, b, c and d are each an integer of 0 to 2.

According to an embodiment, in the compound of the formula 1, $R_1$ to $R_4$ may be each independently hydrogen, methyl, trifluoromethyl, F, Cl or a cyano group, and a, b, c and d may be each an integer of 0 to 2.

According to one embodiment, the diamine compound of formula 1 may be selected from compounds of the following structural formulas, but is not limited thereto.

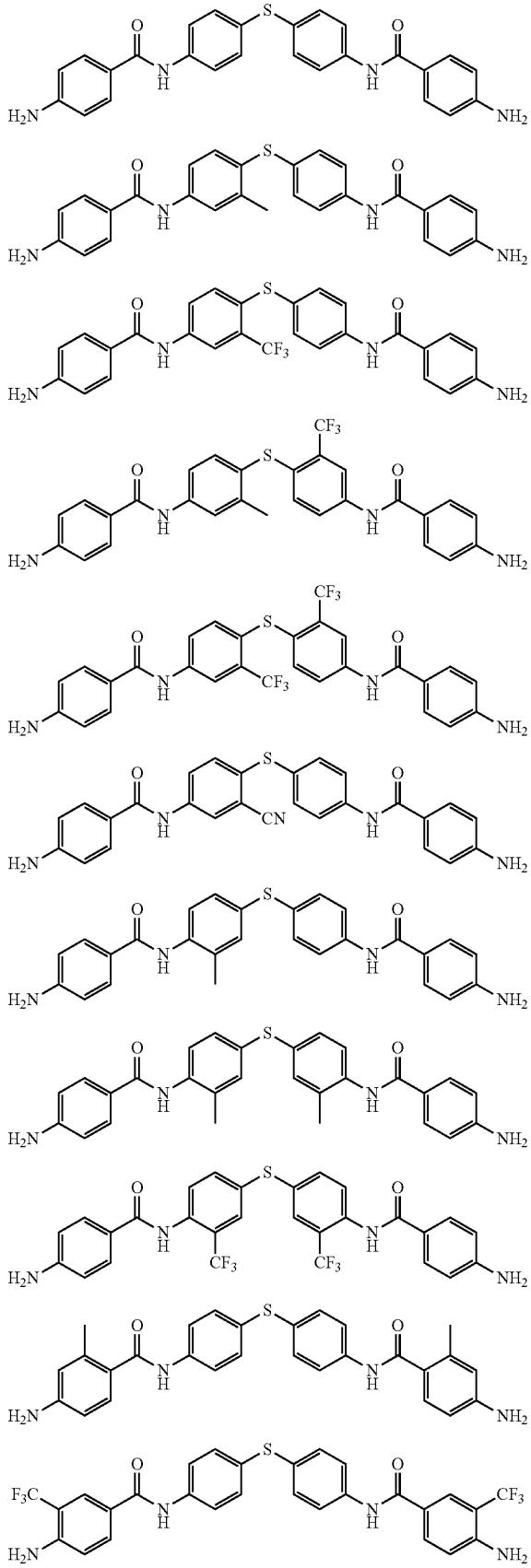

-continued
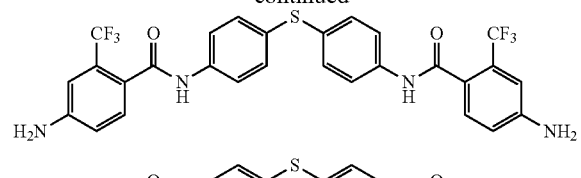
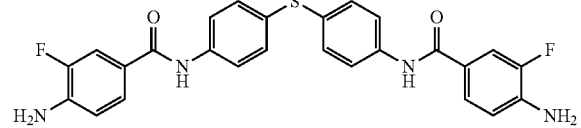
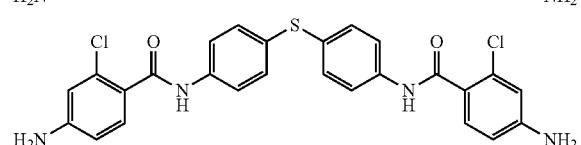
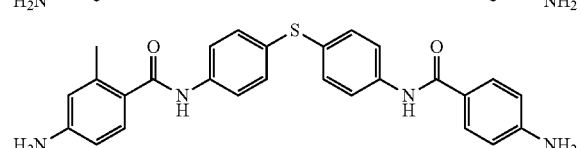
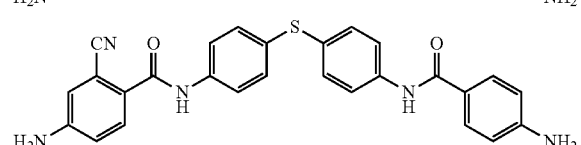
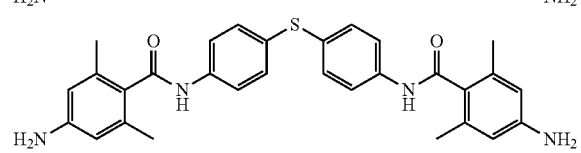
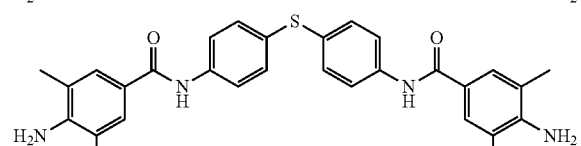
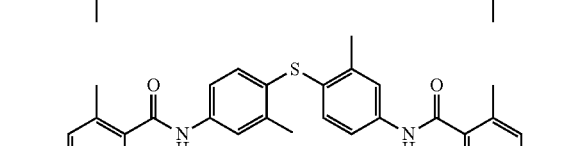
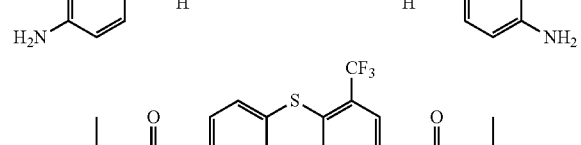
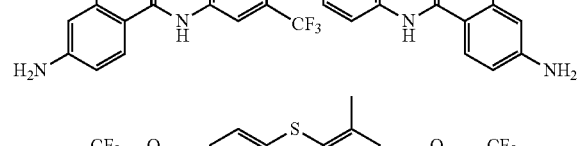
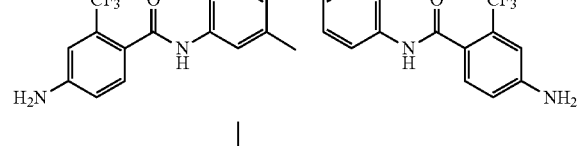
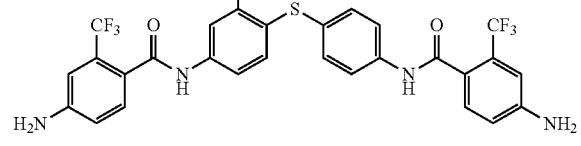
-continued
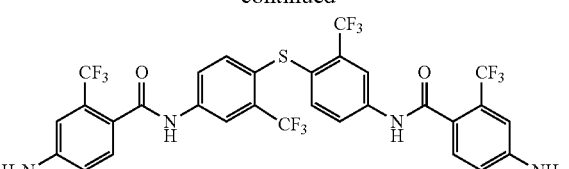
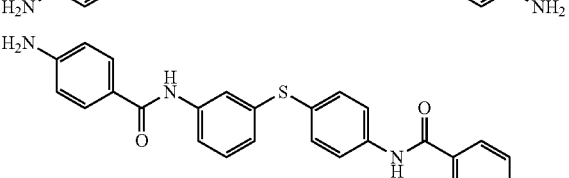
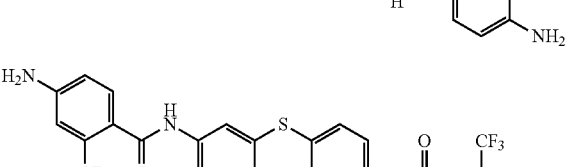
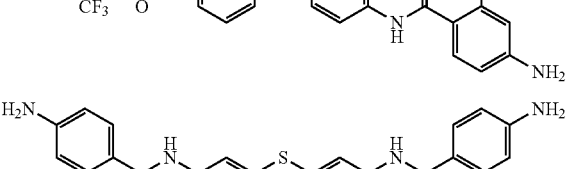
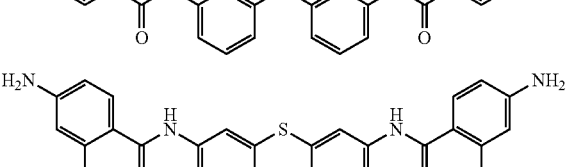
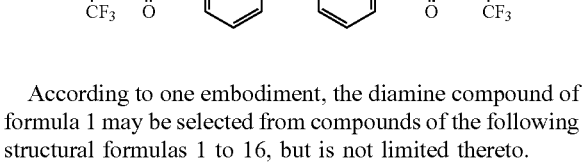
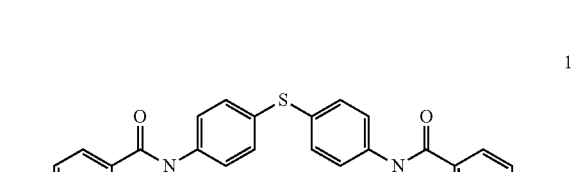
According to one embodiment, the diamine compound of formula 1 may be selected from compounds of the following structural formulas 1 to 16, but is not limited thereto.
1
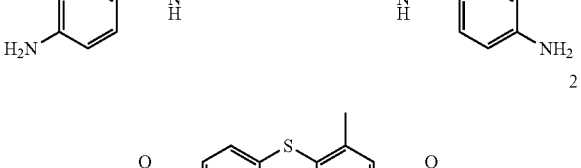
2
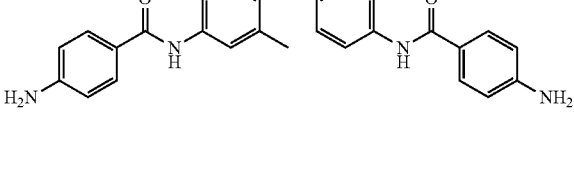
3
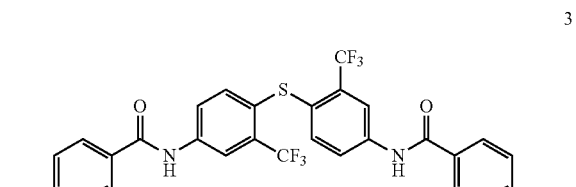

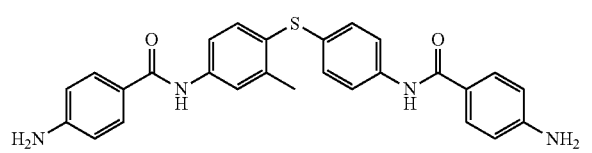

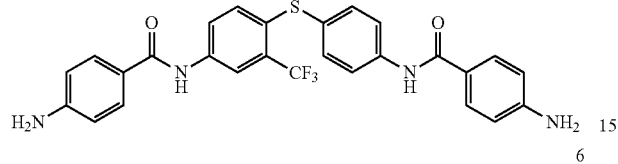

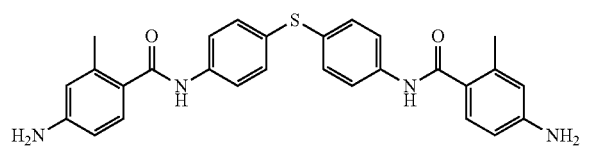

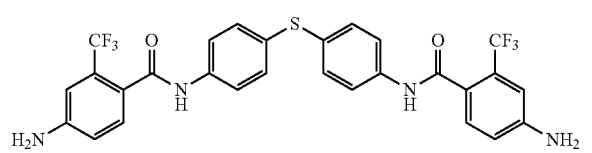

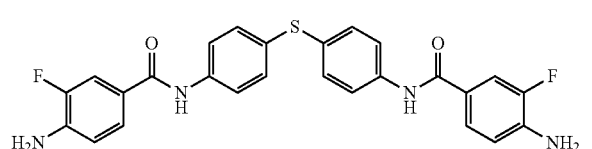

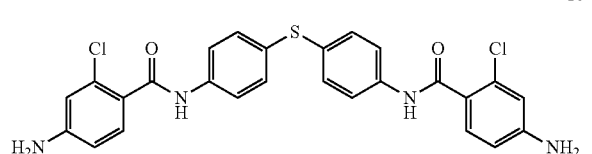

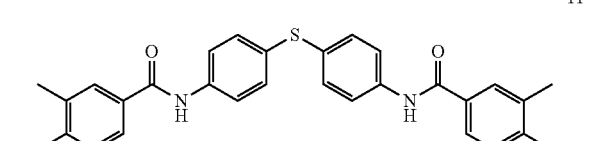

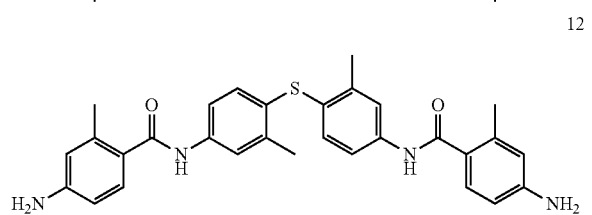

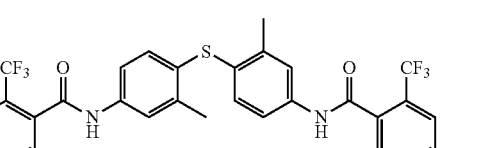

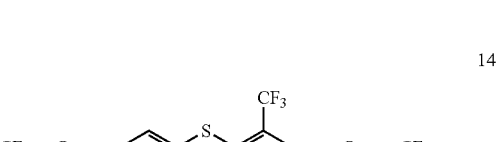

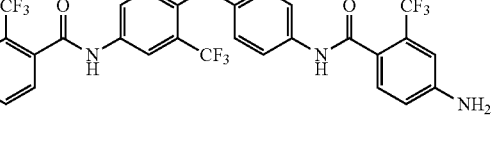

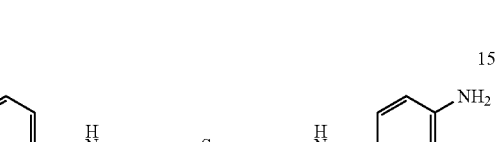

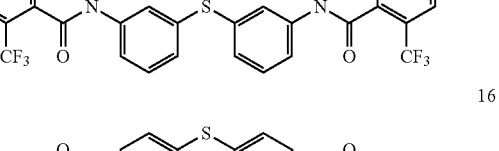

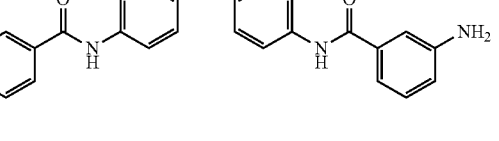

As described above, the diamine compound of the present invention has a structure having amine-substituted phenyl rings located on both sides of the molecule and diphenyl sulfide (introduction of —S—) at the center of the molecule. Therefore, when the diamine compound of the present invention is used as a polymerization component of a polyimide precursor, the film after curing can have improved heat resistance and mechanical properties after curing and an improved refractive index.

The method for preparing the diamine compound of formula 1 according to the present invention is not particularly limited and can be prepared by a synthetic method known to those skilled in the art, for example, according to Reaction Scheme 1 below.

[Reaction Scheme 1]

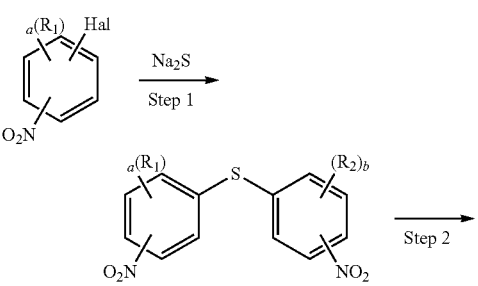

-continued

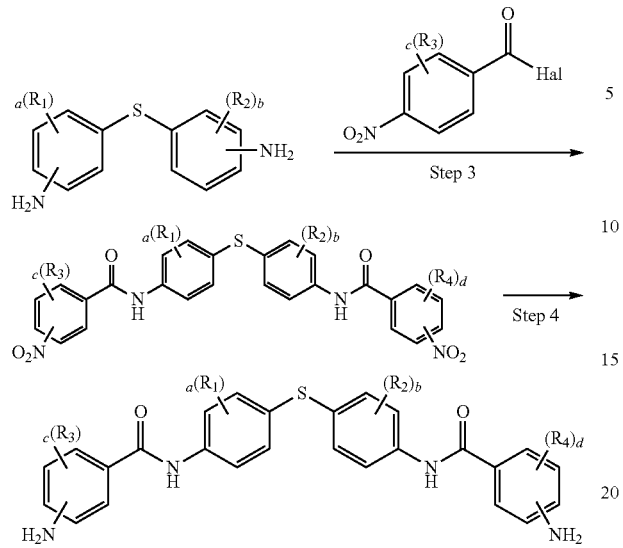

In reaction scheme 1, $R_1$, $R_2$, $R_3$, $R_4$, a, b, c and d are the same as defined in the formula 1, and Hal is a halogen atom.

The step 1 of the reaction scheme 1 may be carried out by reacting the reaction compound in a solvent such as N-methylpyrrolidone or tetrahydrofuran at a high temperature of 180 to 220° C. for 6 to 10 hours, such as for 8 hours.

The steps 2 and 4 of the reaction scheme 1 may be carried out as a reduction reaction by injecting hydrogen gas in the presence of a Pd/C catalyst, wherein ethanol or the like may be used as a solvent.

The step 3 of the reaction scheme 1 may be carried out by reacting the reaction compound at a high temperature of 100 to 130° C. for about 20 hours in the presence of a base such as triethylamine (TEA), wherein toluene may be used as a solvent.

In addition, the present invention provides a polyimide precursor (polyamic acid) prepared by polymerizing a polymerization component including at least one diamine compound and at least one acid dianhydride, wherein the diamine compound comprises the diamine compound of the formula 1. The imidization reaction of the polyimide precursor can be performed to obtain a desired polyimide.

As the acid anhydride used for polymerization reaction, tetracarboxylic dianhydrides may be used, for example. For example, the tetracarboxylic dianhydride includes a tetracarboxylic dianhydride containing aliphatic, alicyclic or aromatic tetravalent organic group(s), or a combination thereof in the molecule, wherein the aliphatic, alicyclic or aromatic tetravalent organic group(s) is connected to each other via a crosslinking structure. Preferably, the tetracarboxylic dianhydride includes an acid dianhydride comprising a structure having a monocyclic or polycyclic aromatic group, a monocyclic or polycyclic alicyclic group, or two or more of them connected by a single bond or a functional group. Alternatively, it may include a tetracarboxylic dianhydride containing a rigid structure, such as a tetravalent organic group having aliphatic ring(s) or aromatic ring(s), in which each ring is a single ring structure, each ring is fused to form a heterocyclic structure, or two or more of the rings are connected to each other by a single bond.

For example, the tetracarboxylic dianhydride may comprise a tetravalent organic group selected from the following formulas 2a to 2e:

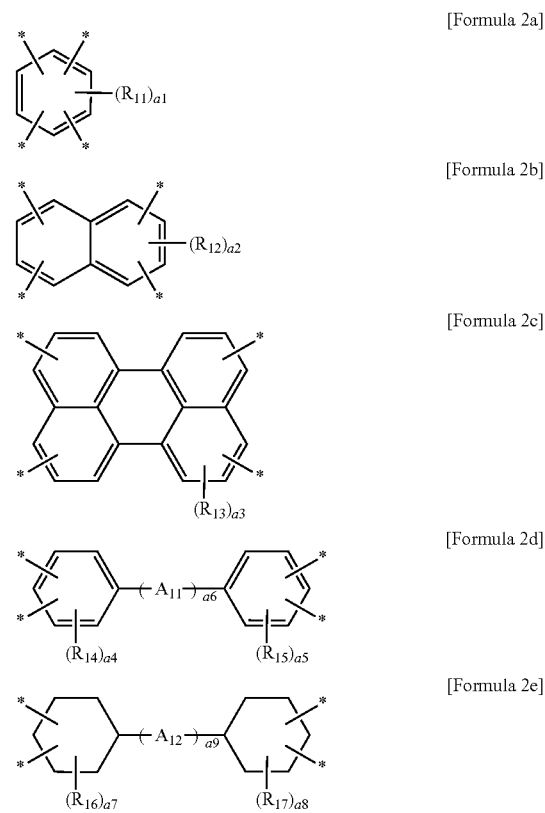

In the formulas 2a to 2e, $R_{11}$ to $R_{17}$ may be each independently selected from a halogen atom selected from F, Cl, Br and I, a hydroxyl group, a thiol group (—SH), a nitro group, a cyano group, an alkyl group having 1 to 10 carbon atoms, a halogenoalkoxy group having 1 to 10 carbon atoms, a halogenoalkyl group having 1 to 10 carbon atoms and an aryl group having 6 to 20 carbon atoms, a1 may be an integer of 0 to 2, a2 may be an integer of 0 to 4, a3, may be an integer of 0 to 8, a4, a5, a6, a7, a8 and a9 may be each independently an integer of 0 to 3, $A_{11}$ and $A_{12}$ may be each independently selected from the group consisting of a single bond, —O—, —CR'R"— (wherein, R' and R" are each independently selected from the group consisting of a hydrogen atom, an alkyl group having 1 to 10 carbon atoms (e.g., methyl group, ethyl group, propyl group, isopropyl group, n-butyl, tert-butyl group, pentyl group, etc.) and a haloalkyl group having 1 to 10 carbon atoms (e.g., trifluoromethyl group, etc.)), —C(=O)—, —C(=O)O—, —C(=O)NH—, —S—, —SO—, —SO₂—, —O[CH₂CH₂O]$_y$— (y is an integer of 1 to 44), —NH(C=O)NH—, —NH(C=O)O—, a monocyclic or polycyclic cycloalkylene group having 6 to 18 carbon atoms (e.g., cyclohexylene group, etc.), a monocyclic or polycyclic arylene group having 6 to 18 carbon atoms (e.g., phenylene group, naphthylene group, fluorenylene group, etc.), and combinations thereof.

In addition, the tetracarboxylic dianhydride may comprise a tetravalent organic group selected from the following formulas 3a to 3n:

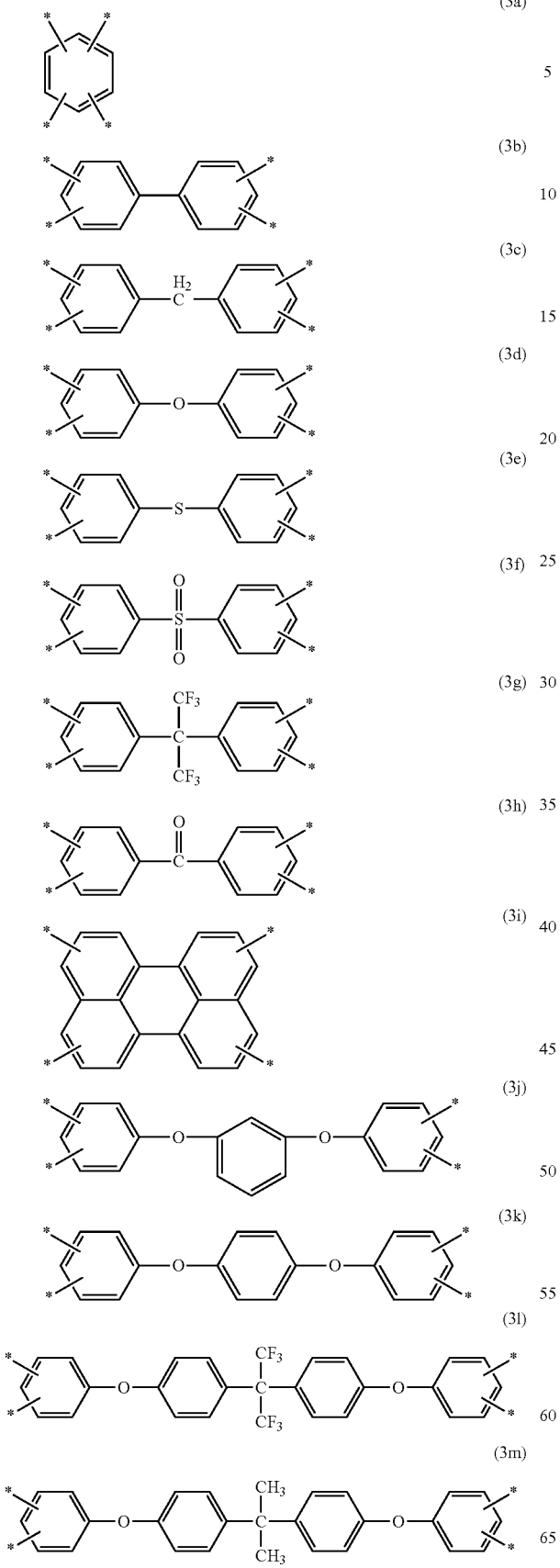

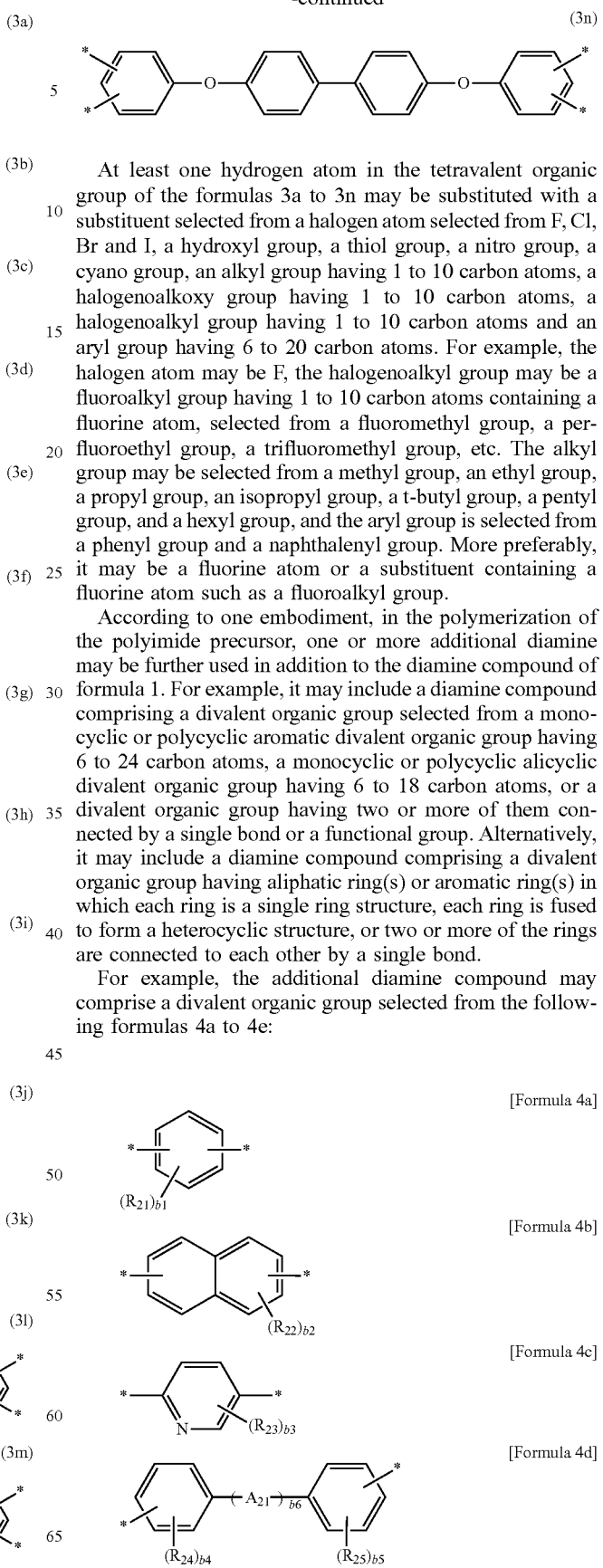

At least one hydrogen atom in the tetravalent organic group of the formulas 3a to 3n may be substituted with a substituent selected from a halogen atom selected from F, Cl, Br and I, a hydroxyl group, a thiol group, a nitro group, a cyano group, an alkyl group having 1 to 10 carbon atoms, a halogenoalkoxy group having 1 to 10 carbon atoms, a halogenoalkyl group having 1 to 10 carbon atoms and an aryl group having 6 to 20 carbon atoms. For example, the halogen atom may be F, the halogenoalkyl group may be a fluoroalkyl group having 1 to 10 carbon atoms containing a fluorine atom, selected from a fluoromethyl group, a perfluoroethyl group, a trifluoromethyl group, etc. The alkyl group may be selected from a methyl group, an ethyl group, a propyl group, an isopropyl group, a t-butyl group, a pentyl group, and a hexyl group, and the aryl group is selected from a phenyl group and a naphthalenyl group. More preferably, it may be a fluorine atom or a substituent containing a fluorine atom such as a fluoroalkyl group.

According to one embodiment, in the polymerization of the polyimide precursor, one or more additional diamine may be further used in addition to the diamine compound of formula 1. For example, it may include a diamine compound comprising a divalent organic group selected from a monocyclic or polycyclic aromatic divalent organic group having 6 to 24 carbon atoms, a monocyclic or polycyclic alicyclic divalent organic group having 6 to 18 carbon atoms, or a divalent organic group having two or more of them connected by a single bond or a functional group. Alternatively, it may include a diamine compound comprising a divalent organic group having aliphatic ring(s) or aromatic ring(s) in which each ring is a single ring structure, each ring is fused to form a heterocyclic structure, or two or more of the rings are connected to each other by a single bond.

For example, the additional diamine compound may comprise a divalent organic group selected from the following formulas 4a to 4e:

[Formula 4e]

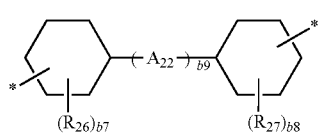

In the formulas 4a to 4e, $R_{21}$ to $R_{27}$ may be each independently selected from a halogen atom selected from F, Cl, Br and I, a hydroxyl group, a thiol group, a nitro group, a cyano group, an alkyl group having 1 to 10 carbon atoms, a halogenoalkoxy group having 1 to 10 carbon atoms, a halogenoalkyl group having 1 to 10 carbon atoms and an aryl group having 6 to 20 carbon atoms, $A_{21}$ and $A_{22}$ may be each independently selected from the group consisting of —O—, —CR'R"— (wherein, R' and R" are each independently selected from the group consisting of a hydrogen atom, an alkyl group having 1 to 10 carbon atoms (e.g., methyl group, ethyl group, propyl group, isopropyl group, n-butyl, tert-butyl group, pentyl group, etc.) and a haloalkyl group having 1 to 10 carbon atoms (e.g., trifluoromethyl group, etc.)), —C(=O)—, —C(=O)O—, —C(=O)NH—, —S—, —SO—, —SO$_2$—, —O[CH$_2$CH$_2$O]$_y$— (y is an integer of 1 to 44), —NH(C=O)NH—, —NH(C=O)O—, a monocyclic or polycyclic cycloalkylene group having 6 to 18 carbon atoms (e.g., cyclohexylene group, etc.), a monocyclic or polycyclic arylene group having 6 to 18 carbon atoms (e.g., phenylene group, naphthalene group, fluorenylene group, etc.), and combinations thereof, b1 is an integer from 0 to 4, b2 is an integer from 0 to 6, b3 is an integer from 0 to 3, b4 and b5 are each independently an integer from 0 to 4, and b7 and b8 are each independently an integer from 0 to 4, and b6 and b9 are each independently an integer from 0 to 3.

For example, the additional diamine compound may comprise a divalent organic group selected from the following formulas 5a to 5p:

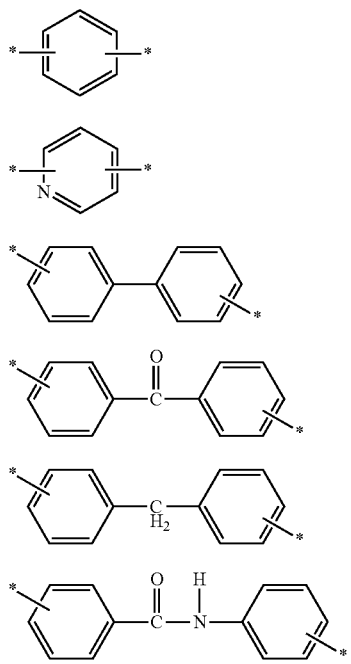

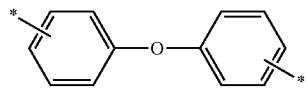

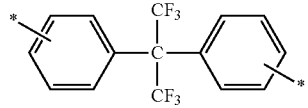

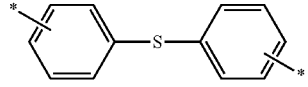

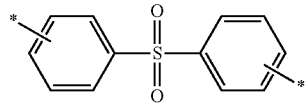

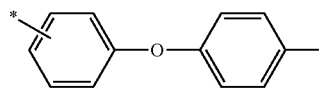

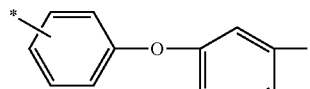

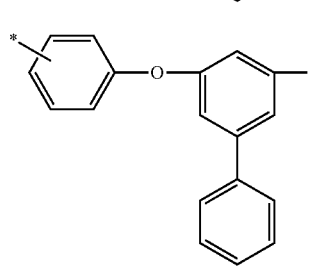

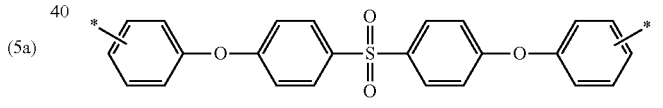

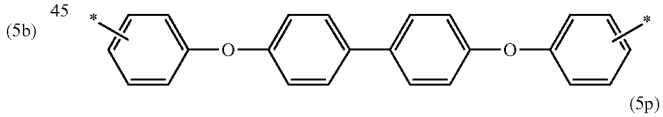

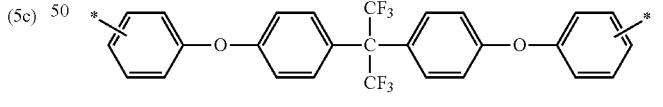

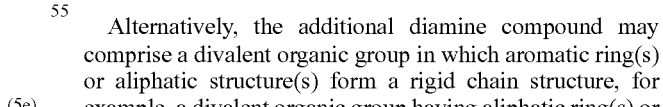

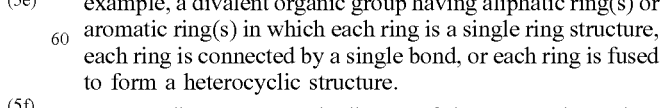

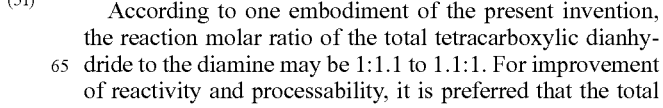

Alternatively, the additional diamine compound may comprise a divalent organic group in which aromatic ring(s) or aliphatic structure(s) form a rigid chain structure, for example, a divalent organic group having aliphatic ring(s) or aromatic ring(s) in which each ring is a single ring structure, each ring is connected by a single bond, or each ring is fused to form a heterocyclic structure.

According to one embodiment of the present invention, the reaction molar ratio of the total tetracarboxylic dianhydride to the diamine may be 1:1.1 to 1.1:1. For improvement of reactivity and processability, it is preferred that the total tetracarboxylic dianhydride is reacted in an excess amount relative to the diamine compound, or that the diamine compound is reacted in an excess amount relative to the total tetracarboxylic dianhydride.

According to one embodiment of the invention, the tetracarboxylic dianhydride and the diamine compound may be reacted in a molar ratio of 1:0.98 to 0.98:1, preferably 1:0.99 to 0.99:1.

The polymerization reaction may be carried out by a conventional polymerization method of a polyimide or a precursor thereof, such as solution polymerization.

The organic solvent that can be used in the polymerization reaction may include ketones such as γ-butyrolactone, 1,3-dimethyl-2-imidazolidinone, methyl ethyl ketone, cyclohexanone, cyclopentanone and 4-hydroxy-4-methyl-2-pentanone; aromatic hydrocarbons such as toluene, xylene and tetramethylbenzene; glycol ethers (Cellosolve) such as ethylene glycol monoethyl ether, ethylene glycol monomethyl ether, ethylene glycol monobutyl ether, diethylene glycol monoethyl ether, diethylene glycol monomethyl ether, diethylene glycol monobutyl ether, propylene glycol monomethyl ether, propylene glycol monoethyl ether, dipropylene glycol diethyl ether and triethylene glycol monoethyl ether; ethyl acetate, butyl acetate, ethylene glycol monoethyl ether acetate, ethylene glycol monobutyl ether acetate, diethylene glycol monoethyl ether acetate, dipropylene glycol monomethyl ether acetate, ethanol, propanol, ethylene glycol, propylene glycol, dimethylpropionamide (DMPA), diethylpropionamide (DEPA), dimethylacetamide (DMAc), N,N-diethylacetamide, dimethylformamide (DMF), diethylformamide (DEF), N-methylpyrrolidone (NMP), N-ethylpyrrolidone (NEP), N,N-dimethylmethoxyacetamide, dimethylsulfoxide, pyridine, dimethylsulfone, hexamethylphosphoramide, tetramethylurea, N-methylcaprolactam, tetrahydrofuran, m-dioxane, p-dioxane, 1,2-dimethoxyethane, bis(2-methoxyethyl)ether, 1,2-bis(2-methoxyethoxy)ethane, bis[2-(2-methoxyethoxy)]ether, Equamide M100 (3-methoxy-N,N-dimethylpropionamide, Idemitsu Kosan Co., Ltd.), Equamide B100 (3-butoxy-N,N-dimethylpropionamide, Idemitsu Kosan Co., Ltd.) and the like, and these solvents may be used alone or as a mixture of two or more.

According to one embodiment, the organic solvent may have a boiling point of 300° C. or less and a positive partition coefficient Log P at 25° C., more specifically, a partition coefficient Log P of 0.01 to 3, or 0.01 to 2, or 0.01 to 1. The partition coefficient can be calculated using an ACD/Log P module of ACD/Percepta platform from ACD/Labs. The ACD/Log P module uses an algorithm based on QSPR (Quantitative Structure-Property Relationship) methodology using 2D molecular structures.

The solvent having a positive partition coefficient Log P refers to a hydrophobic solvent. According to the research of the present inventors, it is found that when the polyimide precursor composition is prepared using a specific solvent having a positive partition coefficient Log P, the edge back phenomenon is improved. In addition, in the present invention it is possible to control the edge back phenomenon of the solution without using additives for controlling surface tension of the material and smoothness of the coating film, such as a leveling agent, by using a solvent having a positive partition coefficient Log P as described above. Since additional additives are not used, it is possible to eliminate quality and process problems such as the presence of low-molecular substances in the final product, as well as more efficiently to form a polyimide film having uniform properties.

For example, in the process of coating the polyimide precursor composition on the glass substrate, an edge back phenomenon may occur due to shrinkage of the coating layer during curing or under the condition of standing the coating solution in a humidity condition. The edge back phenomenon of the coating solution may cause a variation in the thickness of the film. As a result, the film may be cut off or have broken edges when cutting due to a lack of flex resistance of the film, causing problems of poor process workability and reduced yield.

In addition, when fine foreign substances having polarity are introduced into the polyimide precursor composition applied on the substrate, for the polyimide precursor composition including a polar solvent having a negative partition coefficient Log P, sporadic coating cracks or thickness change may occur based on location of the foreign substance due to polarity of the foreign substance. In case of using a hydrophobic solvent having a positive partition coefficient Log P, the occurrence of thickness change due to cracking of the coating may be reduced or suppressed even when fine foreign substances having polarity are introduced.

Specifically, in the polyimide precursor composition including a solvent having a positive Log P, an edge back ratio defined by the following Equation 1 may be 0% to 0.1% or less.

$$\text{Edge back ratio (\%)} = [(A-B)/A] \times 100 \qquad \text{[Equation 1]}$$

wherein,
A: area of the polyimide precursor composition completely coated on the substrate (100 mm×100 mm),
B: area after the edge back phenomenon occurs from the edge of the substrate with the polyimide precursor composition or the polyimide film coated thereon.

The edge back phenomenon of the polyimide precursor composition and the polyimide film may occur within 30 minutes after coating the polyimide precursor composition solution, and particularly, the film may be rolled up from the edge to make the thickness of the edge thicker.

After coating the polyimide precursor composition on a substrate and then standing it at a temperature of 20 to 30° C. and in a humidity condition of 40% or more, more specifically, in a humidity condition of 40% to 80%, that is, in each humidity condition of 40%, 50%, 60%, 70% and 80% for 10 minutes or more, for example 40 minutes or more, the edge back ratio of the coated composition solution may be 0.1% or less, preferable 0.05%, more preferably almost 0%.

The edge back ratio as described above is maintained even after curing by heat treatment, and specifically the edge back ratio may be 0.05% or less, more preferably almost 0%.

By solving this edge back phenomenon, the polyimide precursor composition according to the present invention can obtain a polyimide film having more uniform characteristics, thereby further improving the yield of the manufacturing process.

In addition, the solvent used in the polymerization reaction can have a density of 1 g/cm³ or less as measured by standard ASTM D1475. If the density is more than 1 g/cm³, the relative viscosity may be increased and the process efficiency may be reduced.

The polymerization reaction may be carried out in an inert gas or a nitrogen stream and may be carried out under anhydrous condition.

The reaction temperature during the polymerization reaction may be −20 to 80° C., preferably 0 to 80° C. If the reaction temperature is too high, the reactivity may become high and the molecular weight may become large, and the viscosity of the precursor composition may increase, which may be unfavorable in the process.

The polyimide precursor composition containing polyamic acid may be in the form of a solution dissolved in an organic solvent. For example, when the polyimide precursor is synthesized in an organic solvent, the solution may be the reaction solution as obtained, or may be obtained by diluting this reaction solution with another solvent. When the polyimide precursor is obtained as a solid powder, it may be dissolved in an organic solvent to prepare a solution.

According to one embodiment, the content of the composition may be adjusted by adding an organic solvent such that the total polyimide precursor content is 8 to 25% by weight, preferably 10 to 25% by weight, more preferably 10 to 20% by weight. The polyimide precursor composition may be adjusted to have a viscosity of 3,000 cP or more and 10,000 cP or less, preferably 4,000 cP or more and 9,000 cP or less, more preferably 4,000 cP or more and 8,000 cP or less. When the viscosity of the polyimide precursor composition exceeds 10,000 cP, the efficiency of defoaming during processing of the polyimide film is lowered. It results in not only the lowered efficiency of process but also the deteriorated surface roughness of the produced film due to bubble generation. It may lead to the deteriorated electrical, optical and mechanical properties.

Then, the polyimide precursor resulted from the polymerization reaction may be imidized by chemical or thermal imidization to prepare a transparent polyimide film.

According to one embodiment, the polyimide film may be manufactured by a method comprising:
  applying the polyimide precursor composition onto a carrier substrate; and
  heating and curing the applied polyimide precursor composition.

As the carrier substrate, a glass substrate, a metal substrate, a plastic substrate, or the like can be used without any particular limitation. Among them, a glass substrate may be preferable which is excellent in thermal and chemical stabilities during the imidization and curing process for the polyimide precursor and can be easily separated even without any treatment with additional release agent while not damaging the polyimide film formed after curing.

The applying process may be carried out according to a conventional application method. Specifically, a spin coating method, a bar coating method, a roll coating method, an air knife method, a gravure method, a reverse roll method, a kiss roll method, a doctor blade method, a spray method, a dipping method, a brushing method, or the like may be used. Of these, it is more preferred to carry out by a casting method which allows a continuous process and enables to increase an imidization rate of polyimide.

In addition, the polyimide precursor composition may be applied on the substrate in the thickness range such that the polyimide film to be finally produced has a thickness suitable for a display substrate. For example, it may be applied in an amount such that the film has a thickness of 10 to 30 µm.

After the application of the polyimide precursor composition, a drying process for removing the solvent remained in the polyimide precursor composition may be further optionally performed prior to the curing process.

The drying process may be carried out according to a conventional method. Specifically, the drying process may be carried out at a temperature of 140° C. or lower, or from 80° C. to 140° C. If the drying temperature is lower than 80° C., the drying process becomes longer. If the drying temperature exceeds 140° C., the imidization proceeds rapidly, making it difficult to form a polyimide film having a uniform thickness.

Then, the polyimide precursor composition is applied on a substrate and heat-treated in an IR oven, in a hot air oven, or on a hot plate. The heat treatment temperature may range from 280 to 500° C., preferably from 300 to 450° C. The heat treatment may be performed in a multi-step heating process within the above temperature range. The heat treatment process may be performed for 20 to 70 minutes, and preferably for 20 to 60 minutes.

The residual stress immediately after curing of the polyimide film prepared as described above may be 40 MPa or less, and the residual stress change value after standing the polyimide film at 25° C. and 50% humidity for 3 hours may be 5 MPa or less.

The polyimide film may have a yellowness of 15 or less, and preferably 13 or less. Further, the polyimide film may have a haze of 2% or less, and preferably 1% or less.

In addition, the polyimide film may have a transmittance at 450 nm of 75% or more, a transmittance at 550 nm of 85% or more, and a transmittance at 630 nm of 90% or more. The polyimide film may have high heat resistance, for example, a thermal decomposition temperature (Td_1%) at which 1% of mass loss occurs may be 500° C. or higher.

The polyimide film prepared as described above may have a modulus of 0.1 to 4 GPa. When the modulus (modulus of elasticity) is less than 0.1 GPa, the film has low rigidity and is easily fragile to external impact. When the modulus exceeds 4 GPa, the coverlay film has excellent rigidity, but cannot secure sufficient flexibility.

In addition, the polyimide film may have an elongation of 20% or more, preferably 50% or more, and a tensile strength of 130 MPa or more, preferably 140 MPa or more.

In addition, the polyimide film according to the present invention may have excellent thermal stability against a temperature change. For example, it may have a thermal expansion coefficient of −10 to 100 ppm/° C., preferably from −7 to 90 ppm/° C., more preferably 80 ppm/° C. or less, after n+1 times (n is an integer of at least 0) heating and cooling processes in a temperature range of 100 to 350° C.

In addition, the polyimide film according to the present invention may have a retardation in a thickness direction ($R_{th}$) of −150 nm to +150 nm, preferably −130 nm to +130 nm, thereby exhibiting optical isotropy to improve visual sensibility.

According to one embodiment, the polyimide film may have an adhesive force to a carrier substrate of 5 gf/in or more, and preferably 10 gf/in or more.

In addition, the present invention provides a flexible device comprising the polyimide film as a substrate.

In one embodiment, the flexible device can be manufactured by a method comprising applying the polyimide precursor composition on a carrier substrate and heating it to form a polyimide film, and then forming a device on the polyimide film; and peeling from the carrier substrate the polyimide film having the device formed thereon.

The flexible device may be, for example, a thin film transistor, a liquid crystal display (LCD), an electronic paper, an organic EL display, a plasma display panel (PDP), or an IC card.

Hereinafter, embodiments of the present invention will be described in detail so that those skilled in the art can easily carry out the present invention. The present invention may, however, be embodied in many different forms and should not be construed as limited to the embodiments set forth herein.

SYNTHESIS EXAMPLE 1

Preparation of Compound 1

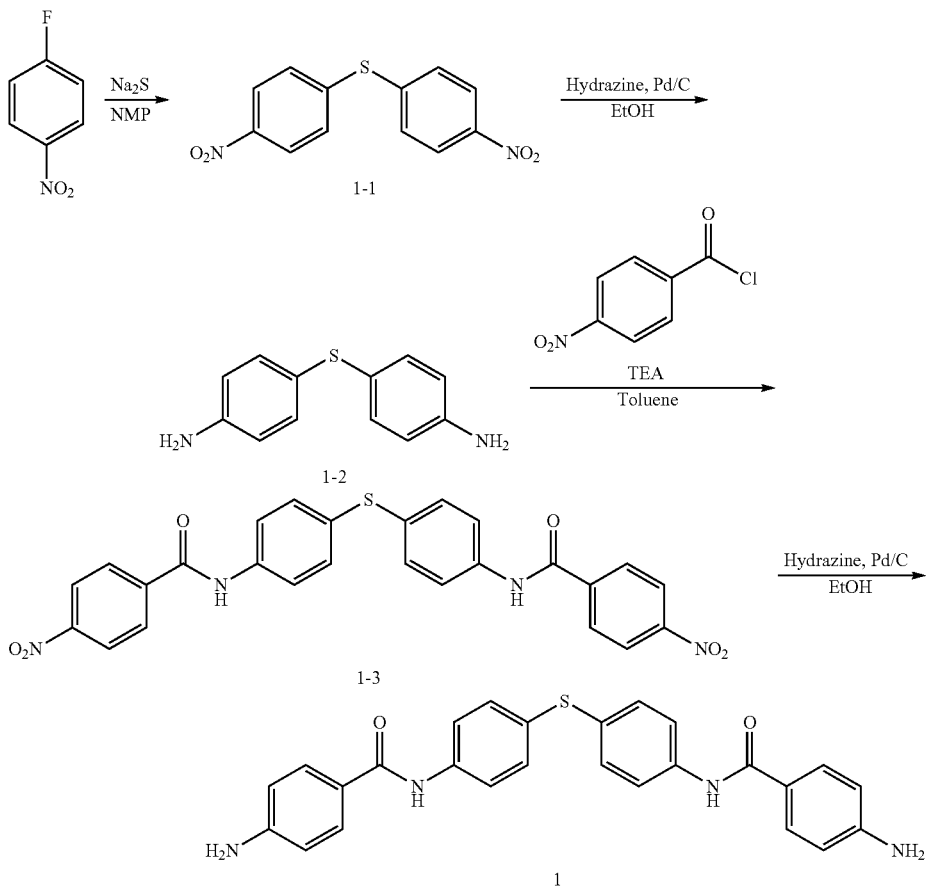

Preparation of Compound 1-1

4-Fluoronitrobenzene (60 g, 425 mmol) and sodium sulfide ($Na_2S$) (16 g, 212 mmol) were heated and stirred for 8 hours at 200° C. in N-methyl-2-pyrrolidone (NMP) solvent (300 mL). After stirring, the reaction was cooled to room temperature, water (600 mL) was poured, and the resulting solid was filtered. The filtered solid was dissolved in ethyl acetate (400 mL) and extracted with water (400 mL). The organic layer was dried over anhydrous magnesium sulfate, and the solvent was dried in a vacuum distillation apparatus. After drying, it was recrystallized in an ethanol solvent (450 mL) to obtain 49 g of compound 1-1 (yield 85%).

Preparation of Compound 1-2

The compound 1-1 (49 g, 177 mmol) and 3 wt % (based on the weight of compound 1-1) of Pd/C catalyst were stirred in an ethanol solvent (300 mL), and then, 80% hydrazine solution (86 mL) was slowly added dropwise to the stirred solution at room temperature and heated and stirred at 100° C. for 12 hours. After stirring, tetrahydrofuran solvent (590 mL) was added to the reactant, and the mixture was filtered over Celite to remove the catalyst. The solvent in the filtrate was dried in a vacuum distillation apparatus. After drying, it was recrystallized in an ethanol solvent (300 mL) to obtain 24 g of compound 1-2 (yield 65%).

Preparation of Compound 1-3

The compound 1-2 (24 g, 111 mmol) and 4-nitrobenzoyl chloride (43 g, 233 mmol) were stirred in a toluene solvent (300 mL) while triethylamine (TEA) (44 g, 444 mmol) was added dropwise to the reactant at room temperature. The mixture was heated and stirred at 120° C. for 20 hours. After stirring, the reaction was cooled to room temperature and extracted with water and ethyl acetate (1:1). The organic layer was dried over anhydrous magnesium sulfate, and the solvent was dried in a vacuum distillation apparatus. After drying, it was recrystallized in an ethanol solvent (400 mL) to obtain 42 g of compound 1-3 (yield 75%).

Preparation of Compound 1

The compound 1-3 (42 g, 81 mmol) and 3 wt % (based on the weight of compound 1-3) of Pd/C catalyst were stirred in an ethanol solvent (300 mL), and then 80% hydrazine solution (39 mL) was slowly added dropwise to the stirred solution at room temperature and heated and stirred at 100° C. for 12 hours. After stirring, tetrahydrofuran solvent (400 mL) was added to the reactant, and the mixture was filtered over Celite to remove the catalyst. The solvent in the filtrate was dried in a vacuum distillation apparatus. After drying, it was recrystallized in an ethanol solvent (350 mL) to obtain 25 g of compound 1 (yield 70%).

HR LC/MS/MS m/z calcd for $C_{26}H_{22}N_4O_2S$ (M+): 454.1463; found: 454.1461

SYNTHESIS EXAMPLE 2

Preparation of Compound 2

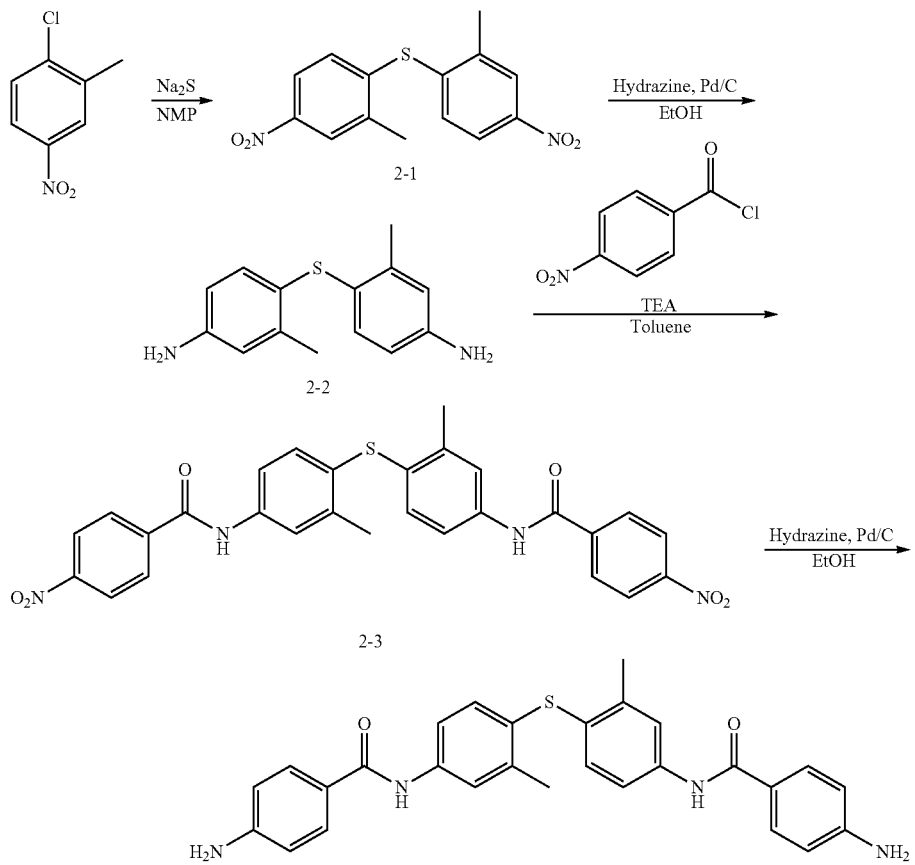

Preparation of Compound 2-1

2-Chloro-5-nitrotoluene (60 g, 350 mmol) and sodium sulfide (Na$_2$S) (13 g, 175 mmol) were heated and stirred for 8 hours at 200° C. in N-methyl-2-pyrrolidone (NMP) solvent (300 mL). After stirring, the reaction was cooled to room temperature, water (600 mL) was poured, and the resulting solid was filtered. The filtered solid was dissolved in ethyl acetate (550 mL) and extracted with water (550 mL). The organic layer was dried over anhydrous magnesium sulfate, and the solvent was dried in a vacuum distillation apparatus. After drying, it was recrystallized in an ethanol solvent (480 mL) to obtain 43 g of compound 2-1 (yield 82%).

Preparation of Compound 2-2

The compound 2-1 (43 g, 141 mmol) and 3 wt % (based on the weight of compound 2-1) of Pd/C catalyst were stirred in an ethanol solvent (440 mL), and then, 80% hydrazine solution (68 mL) was slowly added dropwise to the stirred solution at room temperature and heated and stirred at 100° C. for 12 hours. After stirring, tetrahydrofuran solvent (500 mL) was added to the reactant, and the mixture was filtered over Celite to remove the catalyst. The solvent in the filtrate was dried in a vacuum distillation apparatus. After drying, it was recrystallized in an ethanol solvent (330 mL) to obtain 23 g of compound 2-2 (yield 68%).

Preparation of Compound 2-3

The compound 2-2 (23 g, 94 mmol) and 4-nitrobenzoyl chloride (36 g, 197 mmol) were stirred in a toluene solvent (350 mL) while triethylamine (TEA) (38 g, 376 mmol) was added dropwise to the reactant at room temperature. The mixture was heated and stirred at 120° C. for 20 hours. After stirring, the reaction was cooled to room temperature and extracted with water and ethyl acetate (1:1). The organic layer was dried over anhydrous magnesium sulfate, and the solvent was dried in a vacuum distillation apparatus. After drying, it was recrystallized in an ethanol solvent (420 mL) to obtain 40 g of compound 2-3 (yield 80%).

Preparation of Compound 2

The compound 2-3 (40 g, 73 mmol) and 3 wt % (based on the weight of compound 2-3) of Pd/C catalyst were stirred in an ethanol solvent (340 mL), and then, 80% hydrazine solution (35 mL) was slowly added dropwise to the stirred solution at room temperature and heated and stirred at 100° C. for 12 hours. After stirring, tetrahydrofuran solvent (500 mL) was added to the reactant, and the mixture was filtered over Celite to remove the catalyst. The solvent in the filtrate was dried in a vacuum distillation apparatus. After drying, it was recrystallized in an ethanol solvent (300 mL) to obtain 26 g of compound 2 (yield 75%).

HR LC/MS/MS m/z calcd for $C_{28}H_{26}N_4O_2S$ (M+): 482.1776; found: 482.1779

SYNTHESIS EXAMPLE 3

Preparation of Compound 3

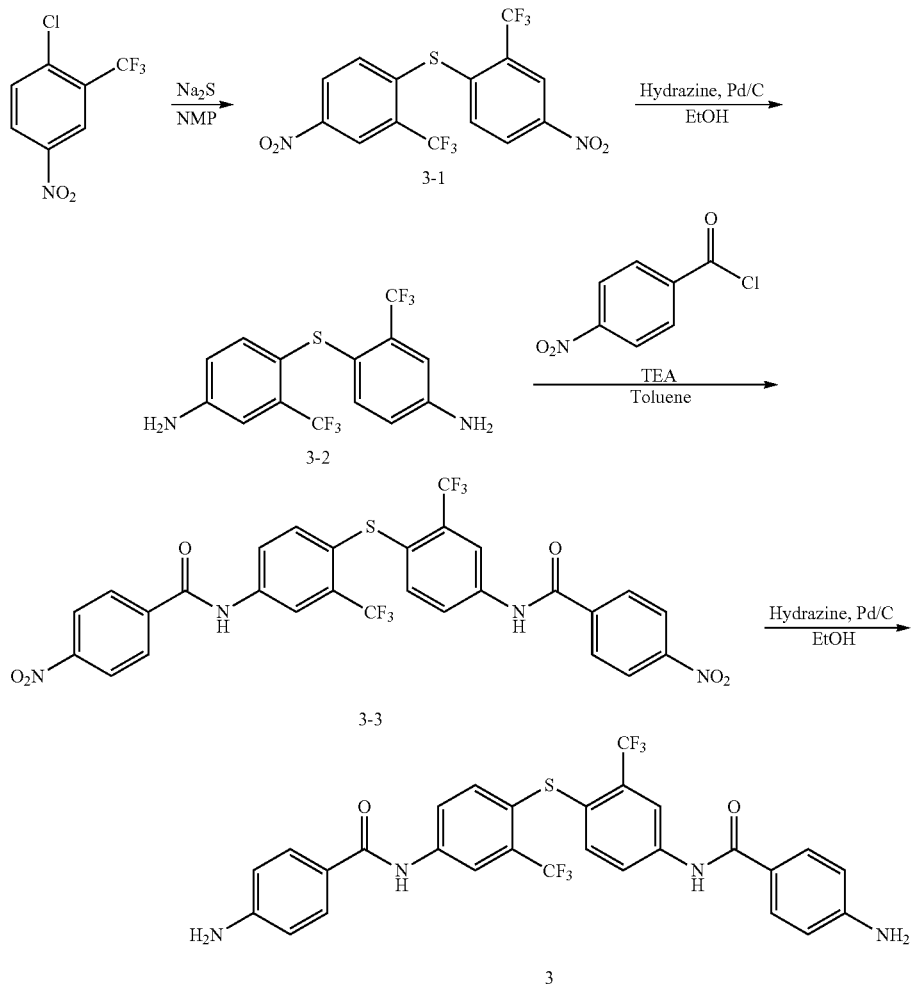

Preparation of Compound 3-1

2-Chloro-5-nitrobenzotrifluoride (60 g, 266 mmol) and sodium sulfide (Na$_2$S) (10 g, 133 mmol) were heated and stirred for 8 hours at 200° C. in N-methyl-2-pyrrolidone (NMP) solvent (460 mL). After stirring, the reaction was cooled to room temperature, water (920 mL) was poured, and the resulting solid was filtered. The filtered solid was dissolved in ethyl acetate (550 mL) and extracted with water (550 mL). The organic layer was dried over anhydrous magnesium sulfate, and the solvent was dried in a vacuum distillation apparatus. After drying, it was recrystallized in an ethanol solvent (460 mL) to obtain 45 g of compound 3-1 (yield 83%).

Preparation of Compound 3-2

The compound 3-1 (45 g, 109 mmol) and 3 wt % (based on the weight of compound 3-1) of Pd/C catalyst were stirred in an ethanol solvent (360 mL), and then, 80% hydrazine solution (53 mL) was slowly added dropwise to the stirred solution at room temperature and heated and stirred at 100° C. for 12 hours. After stirring, tetrahydrofuran solvent (410 mL) was added to the reactant, and the mixture was filtered over Celite to remove the catalyst. The solvent in the filtrate was dried in a vacuum distillation apparatus. After drying, it was recrystallized in an ethanol solvent (320 mL) to obtain 26 g of compound 3-2 (yield 69%).

Preparation of Compound 3-3

The compound 3-2 (26 g, 73 mmol) and 4-nitrobenzoyl chloride (28 g, 155 mmol) were stirred in a toluene solvent (370 mL) while triethylamine (TEA) (29 g, 295 mmol) was added dropwise to the reactant at room temperature. The mixture was heated and stirred at 120° C. for 20 hours. After stirring, the reaction was cooled to room temperature and extracted with water and ethyl acetate (1:1). The organic layer was dried over anhydrous magnesium sulfate, and the solvent was dried in a vacuum distillation apparatus. After drying, it was recrystallized in an ethanol solvent (430 mL) to obtain 39 g of compound 3-3 (yield 83%).

Preparation of Compound 3

The compound 3-3 (39 g, 59 mmol) and 3 wt % (based on the weight of compound 3-3) of Pd/C catalyst were stirred in an ethanol solvent (400 mL), and then, 80% hydrazine solution (29 mL) was slowly added dropwise to the stirred solution at room temperature and heated and stirred at 100° C. for 12 hours. After stirring, tetrahydrofuran solvent (380 mL) was added to the reactant, and the mixture was filtered over Celite to remove the catalyst. The solvent in the filtrate was dried in a vacuum distillation apparatus. After drying, it was recrystallized in an ethanol solvent (300 mL) to obtain 27 g of compound 3 (yield 77%).

HR LC/MS/MS m/z calcd for $C_{28}H_{20}F_6N_4O_2S$ (M+): 590.1211; found: 590.1210

SYNTHESIS EXAMPLE 4

Preparation of Compound 4 hydrazine solution (88 mL) was slowly added dropwise to the stirred solution at room temperature and heated and stirred at 100° C. for 12 hours. After stirring, tetrahydrofuran solvent (400 mL) was added to the reactant, and the mixture was filtered over Celite to remove the catalyst. The solvent in the filtrate was dried in a vacuum distillation apparatus. After drying, it was recrystallized in an ethanol solvent (340 mL) to obtain 27 g of compound 4-2 (yield 66%).

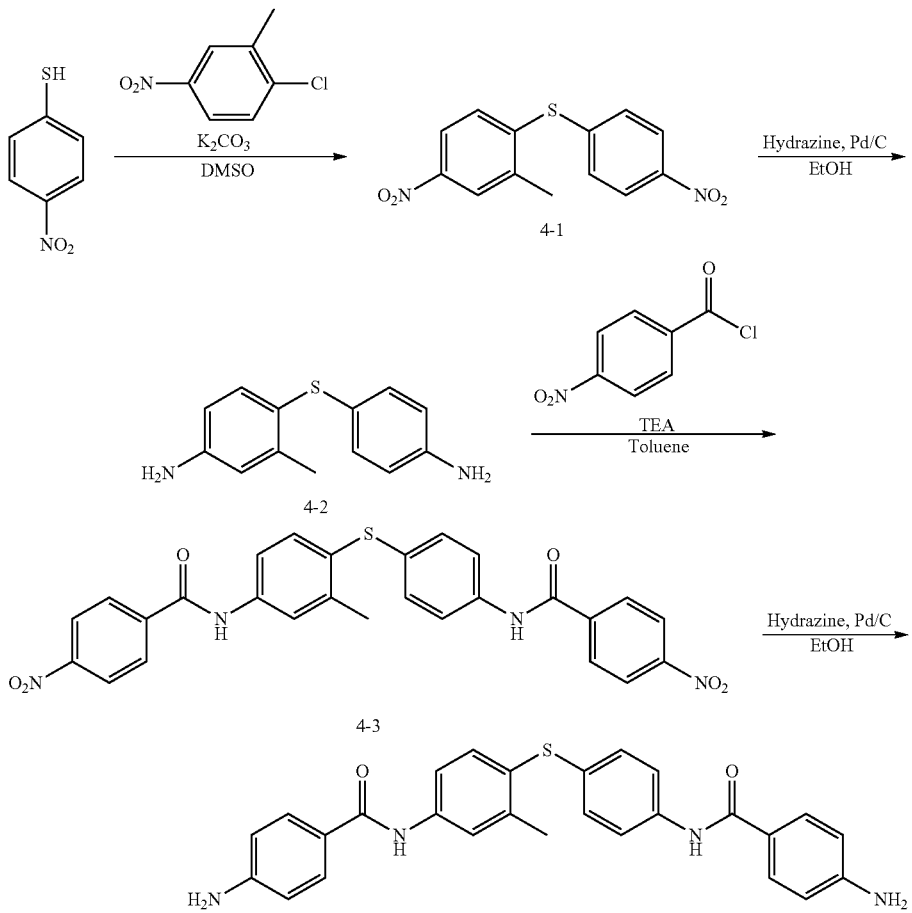

Preparation of Compound 4-1

4-Nitrobenzenethiol (30 g, 193 mmol), 2-chloro-5-nitrotoluene (33 g, 193 mmol) and potassium carbonate (32 g) were heated and stirred for 6 hours at 190° C. in dimethylsulfoxide (DMSO) solvent (400 mL). After stirring, the reaction was cooled to room temperature, water (800 mL) was poured, and the resulting solid was filtered. The filtered solid was dissolved in ethyl acetate (460 mL) and extracted with water (460 mL). The organic layer was dried over anhydrous magnesium sulfate, and the solvent was dried in a vacuum distillation apparatus. After drying, it was recrystallized in an ethanol solvent (500 mL) to obtain 53 g of compound 4-1 (yield 95%).

Preparation of Compound 4-2

The compound 4-1 (53 g, 182 mmol) and 3 wt % (based on the weight of compound 4-1) of Pd/C catalyst were stirred in an ethanol solvent (420 mL), and then, 80%

Preparation of Compound 4-3

The compound 4-2 (27 g, 117 mmol) and 4-nitrobenzoyl chloride (45 g, 246 mmol) were stirred in a toluene solvent (400 mL) while triethylamine (TEA) (47 g, 469 mmol) was added dropwise to the reactant at room temperature. The mixture was heated and stirred at 120° C. for 20 hours. After stirring, the reaction was cooled to room temperature and extracted with water and ethyl acetate (1:1). The organic layer was dried over anhydrous magnesium sulfate, and the solvent was dried in a vacuum distillation apparatus. After drying, it was recrystallized in an ethanol solvent (480 mL) to obtain 47 g of compound 4-3 (yield 76%).

Preparation of Compound 4

The compound 4-3 (47 g, 88 mmol) and 3 wt % (based on the weight of compound 4-3) of Pd/C catalyst were stirred in an ethanol solvent (400 mL), and then, 80% hydrazine solution (43 mL) was slowly added dropwise to the stirred solution at room temperature and heated and stirred at 100° C. for 12 hours. After stirring, tetrahydrofuran solvent (400 mL) was added to the reactant, and the mixture was filtered over Celite to remove the catalyst. The solvent in the filtrate was dried in a vacuum distillation apparatus. After drying, it was recrystallized in an ethanol solvent (300 mL) to obtain 30 g of compound 4 (yield 74%).

HR LC/MS/MS m/z calcd for $C_{27}H_{24}N_4O_2S$ (M+): 468.1620; found: 468.1622

SYNTHESIS EXAMPLE 5

Preparation of Compound 5

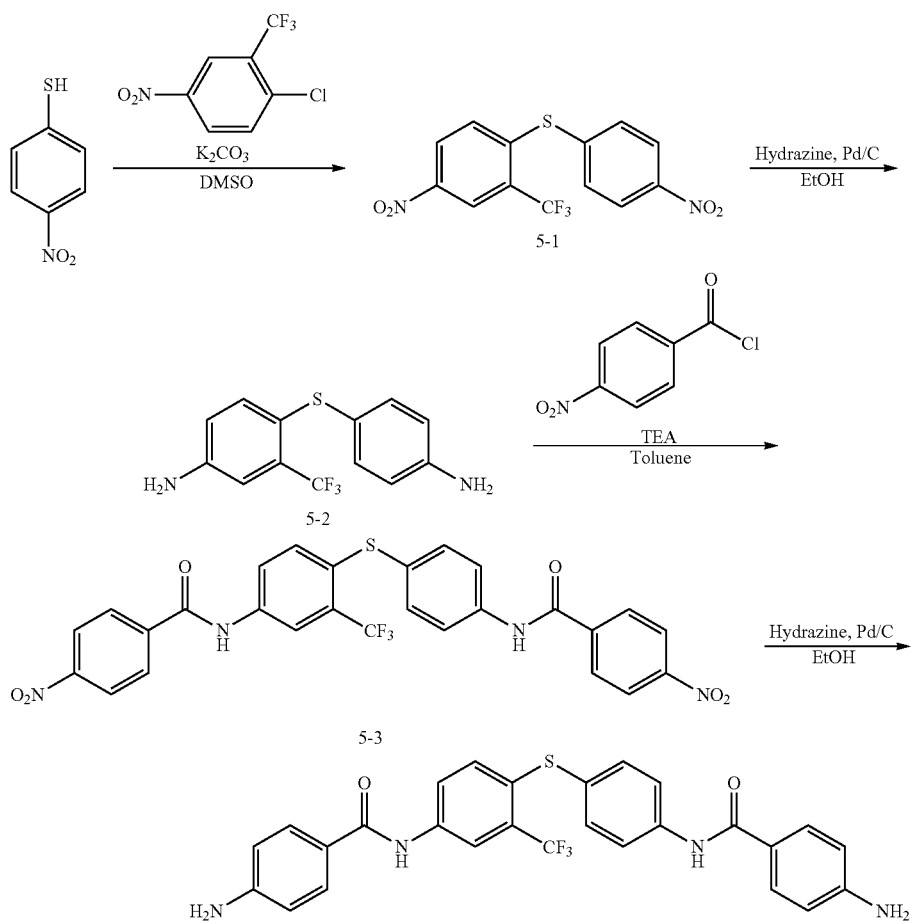

stirred in an ethanol solvent (490 mL), and then, 80% hydrazine solution (76 mL) was slowly added dropwise to the stirred solution at room temperature and heated and stirred at 100° C. for 12 hours. After stirring, tetrahydrofuran solvent (500 mL) was added to the reactant, and the mixture was filtered over Celite to remove the catalyst. The solvent in the filtrate was dried in a vacuum distillation apparatus. After drying, it was recrystallized in an ethanol solvent (300 mL) to obtain 29 g of compound 5-2 (yield 67%).

Preparation of Compound 5-1

4-Nitrobenzenethiol (25 g, 161 mmol), 2-chloro-5-nitrobenzenetrifluoride (36 g, 161 mmol) and potassium carbonate (26 g) were heated and stirred for 6 hours at 190° C. in dimethylsulfoxide (DMSO) solvent (350 mL). After stirring, the reaction was cooled to room temperature, water (700 mL) was poured, and the resulting solid was filtered. The filtered solid was dissolved in ethyl acetate (600 mL) and extracted with water (600 mL). The organic layer was dried over anhydrous magnesium sulfate, and the solvent was dried in a vacuum distillation apparatus. After drying, it was recrystallized in an ethanol solvent (550 mL) to obtain 54 g of compound 5-1 (yield 98%).

Preparation of Compound 5-2

The compound 5-1 (54 g, 156 mmol) and 3 wt % (based on the weight of compound 5-1) of Pd/C catalyst were Preparation of Compound 5-3

The compound 5-2 (29 g, 102 mmol) and 4-nitrobenzoyl chloride (39 g, 214 mmol) were stirred in a toluene solvent (400 mL) while triethylamine (TEA) (41 g, 408 mmol) was added dropwise to the reactant at room temperature. The mixture was heated and stirred at 120° C. for 20 hours. After stirring, the reaction was cooled to room temperature and extracted with water and ethyl acetate (1:1). The organic layer was dried over anhydrous magnesium sulfate, and the solvent was dried in a vacuum distillation apparatus. After drying, it was recrystallized in an ethanol solvent (450 mL) to obtain 48 g of compound 5-3 (yield 82%).

Preparation of Compound 5

The compound 5-3 (48 g, 82 mmol) and 3 wt % (based on the weight of compound 5-3) of Pd/C catalyst were stirred in an ethanol solvent (500 mL), and then, 80% hydrazine solution (40 mL) was slowly added dropwise to the stirred solution at room temperature and heated and stirred at 100°

C. for 12 hours. After stirring, tetrahydrofuran solvent (500 mL) was added to the reactant, and the mixture was filtered over Celite to remove the catalyst. The solvent in the filtrate was dried in a vacuum distillation apparatus. After drying, it was recrystallized in an ethanol solvent (360 mL) to obtain 34 g of compound 5 (yield 80%).

HR LC/MS/MS m/z calcd for $C_{27}H_{21}F_3N_4O_2S$ (M+): 522.1337; found: 522.1334

SYNTHESIS EXAMPLE 6

Preparation of Compound 6

Preparation of Compound 6-2

The compound 6-1 (51 g, 169 mmol) and 3 wt % (based on the weight of compound 6-1) of Pd/C catalyst were stirred in an ethanol solvent (500 mL), and then, 80% hydrazine solution (82 mL) was slowly added dropwise to the stirred solution at room temperature and heated and stirred at 100° C. for 12 hours. After stirring, tetrahydrofuran solvent (500 mL) was added to the reactant, and the mixture was filtered over Celite to remove the catalyst. The solvent in the filtrate was dried in a vacuum distillation apparatus. After drying, it was recrystallized in an ethanol solvent (300 mL) to obtain 26 g of compound 6-2 (yield 65%).

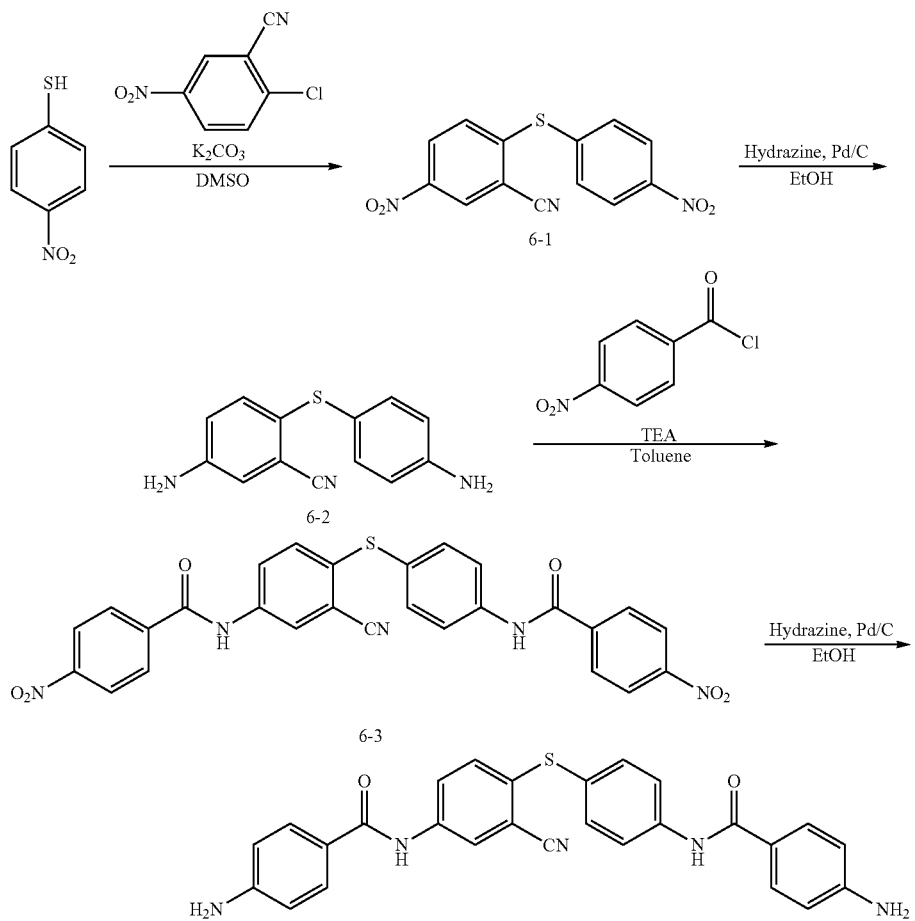

Preparation of Compound 6-1

4-Nitrobenzenethiol (30 g, 193 mmol), 2-chloro-5-nitrobenzonitrile (35 g, 193 mmol) and potassium carbonate (32 g) were heated and stirred for 6 hours at 190° C. in dimethylsulfoxide (DMSO) solvent (400 mL). After stirring, the reaction was cooled to room temperature, water (800 mL) was poured, and the resulting solid was filtered. The filtered solid was dissolved in ethyl acetate (600 mL) and extracted with water (600 mL). The organic layer was dried over anhydrous magnesium sulfate, and the solvent was dried in a vacuum distillation apparatus. After drying, it was recrystallized in an ethanol solvent (500 mL) to obtain 51 g of compound 6-1 (yield 89%).

Preparation of Compound 6-3

The compound 6-2 (26 g, 107 mmol) and 4-nitrobenzoyl chloride (41 g, 226 mmol) were stirred in a toluene solvent (400 mL) while triethylamine (TEA) (43 g, 431 mmol) was added dropwise to the reactant at room temperature. The mixture was heated and stirred at 120° C. for 20 hours. After stirring, the reaction was cooled to room temperature and extracted with water and ethyl acetate (1:1). The organic layer was dried over anhydrous magnesium sulfate, and the solvent was dried in a vacuum distillation apparatus. After drying, it was recrystallized in an ethanol solvent (400 mL) to obtain 44 g of compound 6-3 (yield 76%).

Preparation of Compound 6

The compound 6-3 (44 g, 81 mmol) and 3 wt % (based on the weight of compound 6-3) of Pd/C catalyst were stirred in an ethanol solvent (400 mL), and then, 80% hydrazine solution (39 mL) was slowly added dropwise to the stirred solution at room temperature and heated and stirred at 100° C. for 12 hours. After stirring, tetrahydrofuran solvent (500 mL) was added to the reactant, and the mixture was filtered over Celite to remove the catalyst. The solvent in the filtrate was dried in a vacuum distillation apparatus. After drying, it was recrystallized in an ethanol solvent (300 mL) to obtain 25 g of compound 6 (yield 65%).

HR LC/MS/MS m/z calcd for $C_{27}H_{21}N_5O_2S$ (M+): 479.1416; found: 479.1420

SYNTHESIS EXAMPLE 7

Preparation of Compound 7 stirred in an ethanol solvent (450 mL), and then, 80% hydrazine solution (86 mL) was slowly added dropwise to the stirred solution at room temperature and heated and stirred at 100° C. for 12 hours. After stirring, tetrahydrofuran solvent (400 mL) was added to the reactant, and the mixture was filtered over Celite to remove the catalyst. The solvent in the filtrate was dried in a vacuum distillation apparatus. After drying, it was recrystallized in an ethanol solvent (300 mL) to obtain 24 g of compound 7-2 (yield 65%).

Preparation of Compound 7-3

The compound 7-2 (24 g, 111 mmol) and 2-methyl-4-nitrobenzoyl chloride (46 g, 233 mmol) were stirred in a toluene solvent (300 mL) while triethylamine (TEA) (44 g, 444 mmol) was added dropwise to the reactant at room

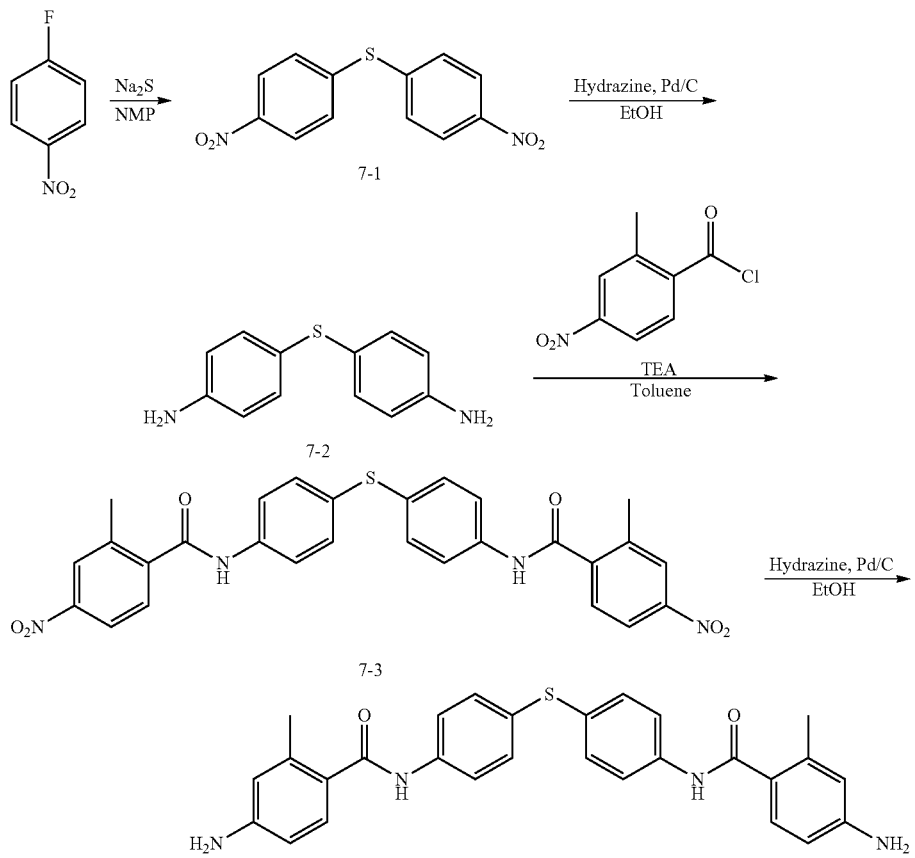

Preparation of Compound 7-1

4-Fluoronitrobenzene (60 g, 425 mmol) and sodium sulfide ($Na_2S$) (16 g, 212 mmol) were heated and stirred for 8 hours at 200° C. in N-methyl-2-pyrrolidone (NMP) solvent (400 mL). After stirring, the reaction was cooled to room temperature, water (800 mL) was poured, and the resulting solid was filtered. The filtered solid was dissolved in ethyl acetate (500 mL) and extracted with water (500 mL). The organic layer was dried over anhydrous magnesium sulfate, and the solvent was dried in a vacuum distillation apparatus. After drying, it was recrystallized in an ethanol solvent (500 mL) to obtain 49 g of compound 7-1 (yield 85%).

Preparation of Compound 7-2

The compound 7-1 (49 g, 177 mmol) and 3 wt % (based on the weight of compound 7-1) of Pd/C catalyst were temperature. The mixture was heated and stirred at 120° C. for 20 hours. After stirring, the reaction was cooled to room temperature and extracted with water and ethyl acetate (1:1). The organic layer was dried over anhydrous magnesium sulfate, and the solvent was dried in a vacuum distillation apparatus. After drying, it was recrystallized in an ethanol solvent (450 mL) to obtain 46 g of compound 7-3 (yield 78%).

Preparation of Compound 7

The compound 7-3 (46 g, 84 mmol) and 3 wt % (based on the weight of compound 7-3) of Pd/C catalyst were stirred in an ethanol solvent (500 mL), and then, 80% hydrazine solution (41 mL) was slowly added dropwise to the stirred solution at room temperature and heated and stirred at 100° C. for 12 hours. After stirring, tetrahydrofuran solvent (400 mL) was added to the reactant, and the mixture was filtered over Celite to remove the catalyst. The solvent in the filtrate was dried in a vacuum distillation apparatus. After drying, it was recrystallized in an ethanol solvent (300 mL) to obtain 29 g of compound 7 (yield 73%).

HR LC/MS/MS m/z calcd for $C_{28}H_{26}N_4O_2S$ (M+): 482.1776; found: 482.1777

SYNTHESIS EXAMPLE 8

Preparation of Compound 8 the stirred solution at room temperature and heated and stirred at 100° C. for 12 hours. After stirring, tetrahydrofuran solvent (400 mL) was added to the reactant, and the mixture was filtered over Celite to remove the catalyst. The solvent in the filtrate was dried in a vacuum distillation apparatus. After drying, it was recrystallized in an ethanol solvent (250 mL) to obtain 16 g of compound 8-2 (yield 65%).

Preparation of Compound 8-3

The compound 8-2 (16 g, 74 mmol) and 4-nitro-2-(trifluoromethyl)benzoyl chloride (39 g, 155 mmol) were stirred in a toluene solvent (400 mL) while triethylamine (TEA) (29

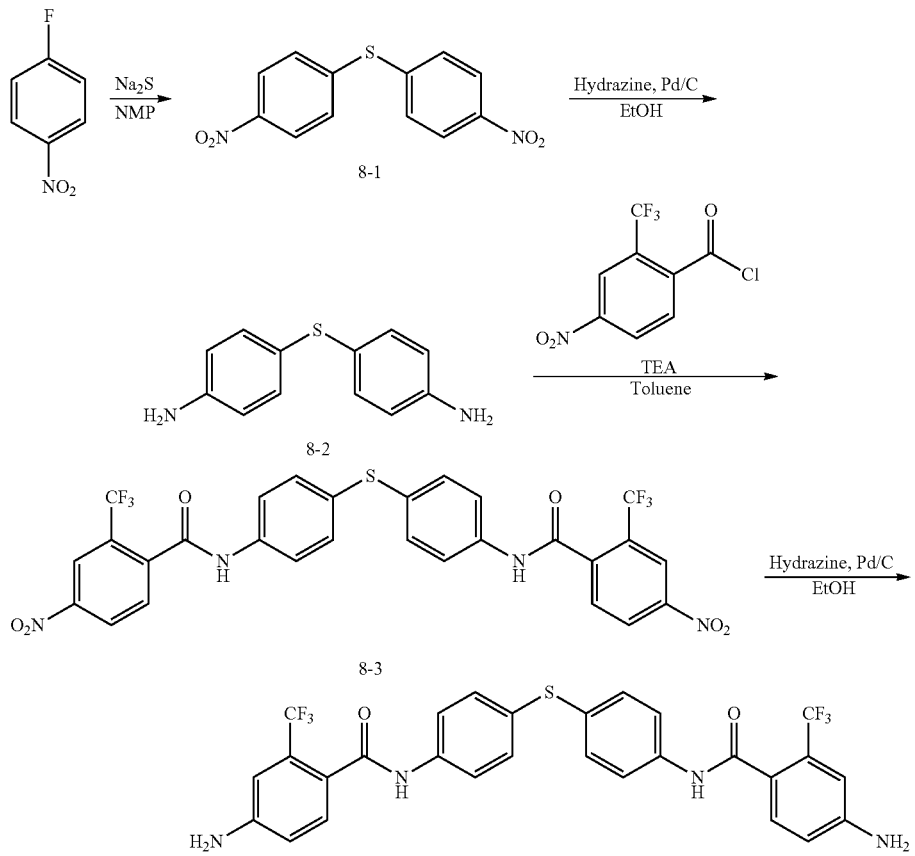

Preparation of Compound 8-1

4-Fluoronitrobenzene (40 g, 283 mmol) and sodium sulfide ($Na_2S$) (11 g, 141 mmol) were heated and stirred for 8 hours at 200° C. in N-methyl-2-pyrrolidone (NMP) solvent (400 mL). After stirring, the reaction was cooled to room temperature, water (800 mL) was poured, and the resulting solid was filtered. The filtered solid was dissolved in ethyl acetate (500 mL) and extracted with water (500 mL). The organic layer was dried over anhydrous magnesium sulfate, and the solvent was dried in a vacuum distillation apparatus. After drying, it was recrystallized in an ethanol solvent (400 mL) to obtain 33 g of compound 8-1 (yield 85%).

Preparation of Compound 8-2

The compound 8-1 (33 g, 119 mmol) and 3 wt % (based on the weight of compound 8-1) of Pd/C catalyst were stirred in an ethanol solvent (380 mL), and then, 80% hydrazine solution (58 mL) was slowly added dropwise to g, 296 mmol) was added dropwise to the reactant at room temperature. The mixture was heated and stirred at 120° C. for 20 hours. After stirring, the reaction was cooled to room temperature and extracted with water and ethyl acetate (1:1). The organic layer was dried over anhydrous magnesium sulfate, and the solvent was dried in a vacuum distillation apparatus. After drying, it was recrystallized in an ethanol solvent (400 mL) to obtain 39 g of compound 8-3 (yield 82%).

Preparation of Compound 8

The compound 8-3 (39 g, 59 mmol) and 3 wt % (based on the weight of compound 8-3) of Pd/C catalyst were stirred in an ethanol solvent (400 mL), and then, 80% hydrazine solution (29 mL) was slowly added dropwise to the stirred solution at room temperature and heated and stirred at 100° C. for 12 hours. After stirring, tetrahydrofuran solvent (400 mL) was added to the reactant, and the mixture was filtered over Celite to remove the catalyst. The solvent in the filtrate was dried in a vacuum distillation apparatus. After drying, it was recrystallized in an ethanol solvent (250 mL) to obtain 28 g of compound 8 (yield 80%).

HR LC/MS/MS m/z calcd for $C_{28}H_{20}F_6N_4O_2S$ (M+): 590.1211; found: 590.1210

SYNTHESIS EXAMPLE 9

Preparation of Compound 9

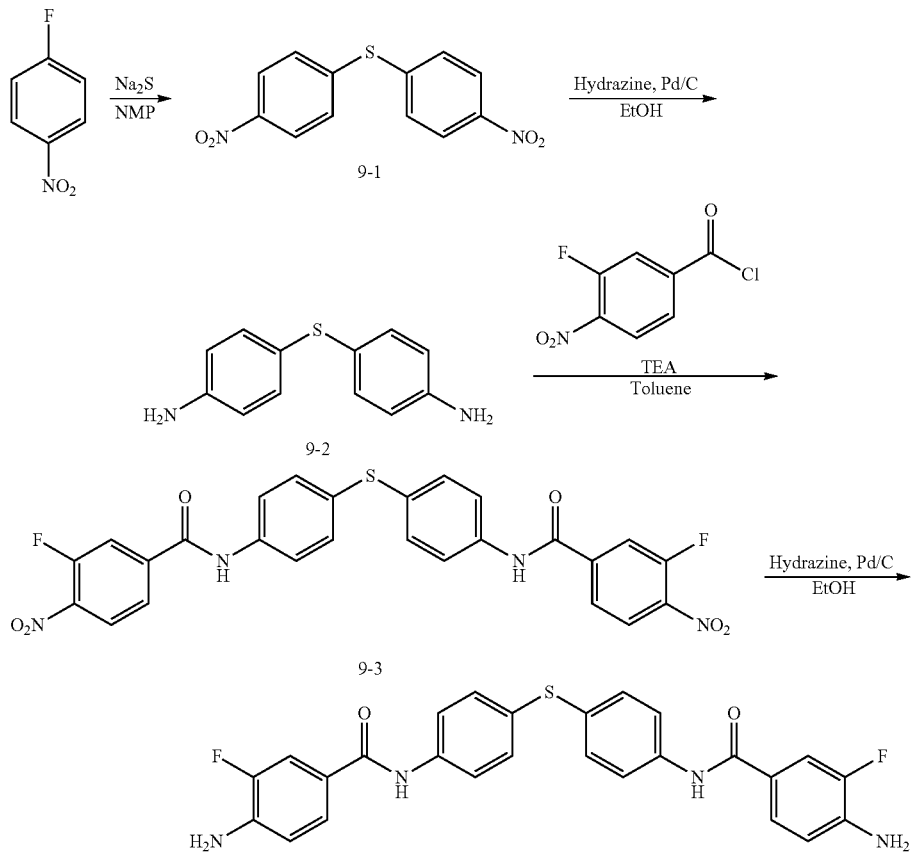

Preparation of Compound 9-1

4-Fluoronitrobenzene (50 g, 354 mmol) and sodium sulfide ($Na_2S$) (13 g, 177 mmol) were heated and stirred for 8 hours at 200° C. in N-methyl-2-pyrrolidone (NMP) solvent (300 mL). After stirring, the reaction was cooled to room temperature, water (600 mL) was poured, and the resulting solid was filtered. The filtered solid was dissolved in ethyl acetate (500 mL) and extracted with water (500 mL). The organic layer was dried over anhydrous magnesium sulfate, and the solvent was dried in a vacuum distillation apparatus. After drying, it was recrystallized in an ethanol solvent (400 mL) to obtain 41 g of compound 9-1 (yield 85%).

Preparation of Compound 9-2

The compound 9-1 (41 g, 148 mmol) and 3 wt % (based on the weight of compound 9-1) of Pd/C catalyst were stirred in an ethanol solvent (400 mL), and then, 80% hydrazine solution (72 mL) was slowly added dropwise to the stirred solution at room temperature and heated and stirred at 100° C. for 12 hours. After stirring, tetrahydrofuran solvent (400 mL) was added to the reactant, and the mixture was filtered over Celite to remove the catalyst. The solvent in the filtrate was dried in a vacuum distillation apparatus. After drying, it was recrystallized in an ethanol solvent (260 mL) to obtain 20 g of compound 9-2 (yield 65%).

Preparation of Compound 9-3

The compound 9-2 (20 g, 92 mmol) and 3-fluoro-4-nitrobenzoyl chloride (39 g, 194 mmol) were stirred in a toluene solvent (400 mL) while triethylamine (TEA) (37 g, 370 mmol) was added dropwise to the reactant at room temperature. The mixture was heated and stirred at 120° C. for 20 hours. After stirring, the reaction was cooled to room temperature and extracted with water and ethyl acetate (1:1). The organic layer was dried over anhydrous magnesium sulfate, and the solvent was dried in a vacuum distillation apparatus. After drying, it was recrystallized in an ethanol solvent (400 mL) to obtain 40 g of compound 9-3 (yield 80%).

Preparation of Compound 9

The compound 9-3 (40 g, 72 mmol) and 3 wt % (based on the weight of compound 9-3) of Pd/C catalyst were stirred in an ethanol solvent (400 mL), and then, 80% hydrazine solution (35 mL) was slowly added dropwise to the stirred solution at room temperature and heated and stirred at 100° C. for 12 hours. After stirring, tetrahydrofuran solvent (400 mL) was added to the reactant, and the mixture was filtered over Celite to remove the catalyst. The solvent in the filtrate was dried in a vacuum distillation apparatus. After drying, it was recrystallized in an ethanol solvent (300 mL) to obtain 27 g of compound 9 (yield 77%).

HR LC/MS/MS m/z calcd for $C_{26}H_{20}F_2N_4O_2S$ (M+): 490.1275; found: 490.1271

SYNTHESIS EXAMPLE 10

Preparation of Compound 10

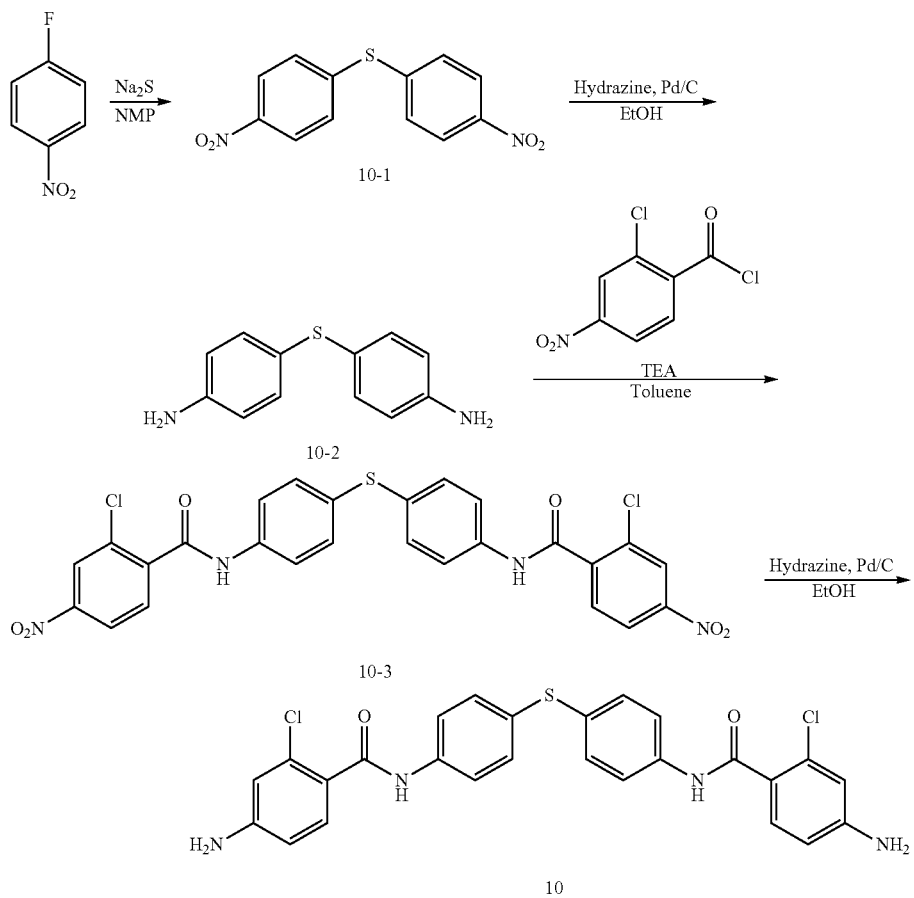

Preparation of Compound 10-1

4-Fluoronitrobenzene (40 g, 283 mmol) and sodium sulfide ($Na_2S$) (14 g, 141 mmol) were heated and stirred for 8 hours at 200° C. in N-methyl-2-pyrrolidone (NMP) solvent (400 mL). After stirring, the reaction was cooled to room temperature, water (800 mL) was poured, and the resulting solid was filtered. The filtered solid was dissolved in ethyl acetate (500 mL) and extracted with water (500 mL). The organic layer was dried over anhydrous magnesium sulfate, and the solvent was dried in a vacuum distillation apparatus. After drying, it was recrystallized in an ethanol solvent (350 mL) to obtain 33 g of compound 10-1 (yield 85%).

Preparation of Compound 10-2

The compound 10-1 (33 g, 119 mmol) and 3 wt % (based on the weight of compound 10-1) of Pd/C catalyst were stirred in an ethanol solvent (370 mL), and then, 80% hydrazine solution (58 mL) was slowly added dropwise to the stirred solution at room temperature and heated and stirred at 100° C. for 12 hours. After stirring, tetrahydrofuran solvent (400 mL) was added to the reactant, and the mixture was filtered over Celite to remove the catalyst. The solvent in the filtrate was dried in a vacuum distillation apparatus. After drying, it was recrystallized in an ethanol solvent (230 mL) to obtain 16 g of compound 10-2 (yield 65%).

Preparation of Compound 10-3

The compound 10-2 (16 g, 74 mmol) and 2-chloro-4-nitrobenzoyl chloride (34 g, 155 mmol) were stirred in a toluene solvent (350 mL) while triethylamine (TEA) (29 g, 296 mmol) was added dropwise to the reactant at room temperature. The mixture was heated and stirred at 120° C. for 20 hours. After stirring, the reaction was cooled to room temperature and extracted with water and ethyl acetate (1:1). The organic layer was dried over anhydrous magnesium sulfate, and the solvent was dried in a vacuum distillation apparatus. After drying, it was recrystallized in an ethanol solvent (300 mL) to obtain 31 g of compound 10-3 (yield 74%).

Preparation of Compound 10

The compound 10-3 (31 g, 53 mmol) and 3 wt % (based on the weight of compound 10-3) of Pd/C catalyst were stirred in an ethanol solvent (320 mL), and then, 80% hydrazine solution (25 mL) was slowly added dropwise to the stirred solution at room temperature and heated and stirred at 100° C. for 12 hours. After stirring, tetrahydrofuran solvent (300 mL) was added to the reactant, and the mixture was filtered over Celite to remove the catalyst. The solvent in the filtrate was dried in a vacuum distillation apparatus. After drying, it was recrystallized in an ethanol solvent (260 mL) to obtain 20 g of compound 10 (yield 72%).

HR LC/MS/MS m/z calcd for $C_{26}H_{20}Cl_2N_6O_2S$ (M+): 522.0684; found: 522.0685

SYNTHESIS EXAMPLE 11

Preparation of Compound 11

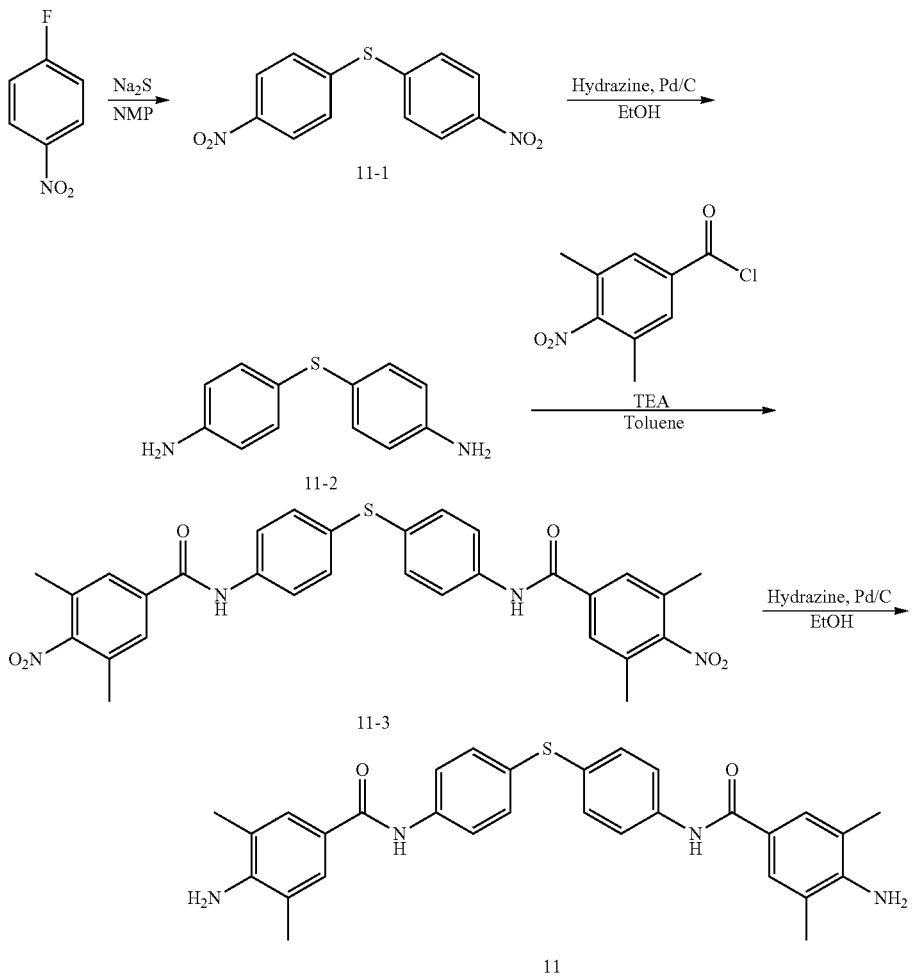

Preparation of Compound 11-1

4-Fluoronitrobenzene (40 g, 283 mmol) and sodium sulfide ($Na_2S$) (11 g, 141 mmol) were heated and stirred for 8 hours at 200° C. in N-methyl-2-pyrrolidone (NMP) solvent (370 mL). After stirring, the reaction was cooled to room temperature, water (740 mL) was poured, and the resulting solid was filtered. The filtered solid was dissolved in ethyl acetate (450 mL) and extracted with water (450 mL). The organic layer was dried over anhydrous magnesium sulfate, and the solvent was dried in a vacuum distillation apparatus. After drying, it was recrystallized in an ethanol solvent (300 mL) to obtain 33 g of compound 11-1 (yield 85%).

Preparation of Compound 11-2

The compound 11-1 (33 g, 119 mmol) and 3 wt % (based on the weight of compound 11-1) of Pd/C catalyst were stirred in an ethanol solvent (350 mL), and then, 80% hydrazine solution (58 mL) was slowly added dropwise to the stirred solution at room temperature and heated and stirred at 100° C. for 12 hours. After stirring, tetrahydrofuran solvent (300 mL) was added to the reactant, and the mixture was filtered over Celite to remove the catalyst. The solvent in the filtrate was dried in a vacuum distillation apparatus. After drying, it was recrystallized in an ethanol solvent (240 mL) to obtain 16 g of compound 11-2 (yield 65%).

Preparation of Compound 11-3

The compound 11-2 (16 g, 74 mmol) and 3,5-dimethyl-4-nitrobenzoyl chloride (33 g, 155 mmol) were stirred in a toluene solvent (350 mL) while triethylamine (TEA) (29 g, 296 mmol) was added dropwise to the reactant at room temperature. The mixture was heated and stirred at 120° C. for 20 hours. After stirring, the reaction was cooled to room temperature and extracted with water and ethyl acetate (1:1). The organic layer was dried over anhydrous magnesium sulfate, and the solvent was dried in a vacuum distillation apparatus. After drying, it was recrystallized in an ethanol solvent (360 mL) to obtain 33 g of compound 11-3 (yield 80%).

Preparation of Compound 11

The compound 11-3 (33 g, 57 mmol) and 3 wt % (based on the weight of compound 11-3) of Pd/C catalyst were stirred in an ethanol solvent (410 mL), and then, 80% hydrazine solution (28 mL) was slowly added dropwise to the stirred solution at room temperature and heated and stirred at 100° C. for 12 hours. After stirring, tetrahydrofuran solvent (400 mL) was added to the reactant, and the mixture was filtered over Celite to remove the catalyst. The solvent in the filtrate was dried in a vacuum distillation apparatus. After drying, it was recrystallized in an ethanol solvent (310 mL) to obtain 22 g of compound 11 (yield 77%).

HR LC/MS/MS m/z calcd for $C_{30}H_{30}N_4O_2S$ (M+): 510.2089 found: 510.2090

SYNTHESIS EXAMPLE 12

Preparation of Compound 12

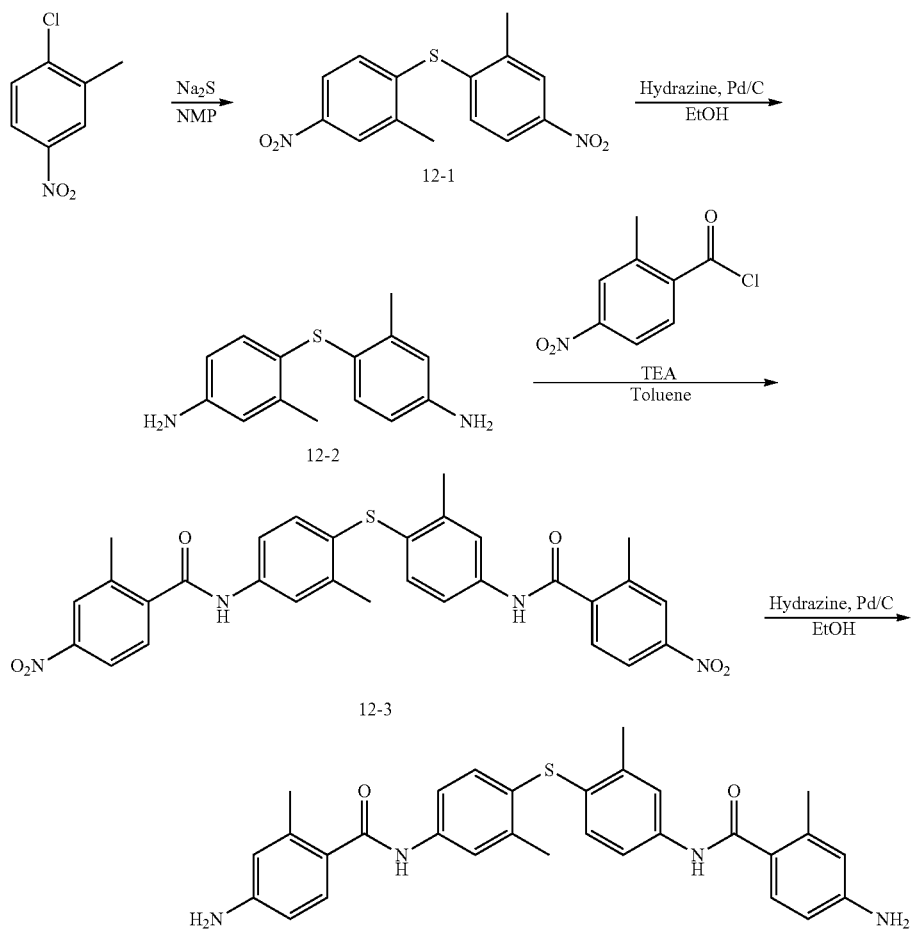

stirred at 100° C. for 12 hours. After stirring, tetrahydrofuran solvent (400 mL) was added to the reactant, and the mixture was filtered over Celite to remove the catalyst. The solvent in the filtrate was dried in a vacuum distillation apparatus. After drying, it was recrystallized in an ethanol solvent (260 mL) to obtain 23 g of compound 12-2 (yield 68%).

Preparation of Compound 12-1

2-Chloro-5-nitrotoluene (60 g, 350 mmol) and sodium sulfide ($Na_2S$) (13 g, 175 mmol) were heated and stirred for 8 hours at 200° C. in N-methyl-2-pyrrolidone (NMP) solvent (460 mL). After stirring, the reaction was cooled to room temperature, water (920 mL) was poured, and the resulting solid was filtered. The filtered solid was dissolved in ethyl acetate (500 mL) and extracted with water (500 mL). The organic layer was dried over anhydrous magnesium sulfate, and the solvent was dried in a vacuum distillation apparatus. After drying, it was recrystallized in an ethanol solvent (470 mL) to obtain 43 g of compound 12-1 (yield 81%).

Preparation of Compound 12-2

The compound 12-1 (43 g, 141 mmol) and 3 wt % (based on the weight of compound 12-1) of Pd/C catalyst were stirred in an ethanol solvent (430 mL), and then, 80% hydrazine solution (68 mL) was slowly added dropwise to the stirred solution at room temperature and heated and Preparation of Compound 12-3

The compound 12-2 (23 g, 94 mmol) and 2-methyl-4-nitrobenzoyl chloride (39 g, 197 mmol) were stirred in a toluene solvent (380 mL) while triethylamine (TEA) (38 g, 376 mmol) was added dropwise to the reactant at room temperature. The mixture was heated and stirred at 120° C. for 20 hours. After stirring, the reaction was cooled to room temperature and extracted with water and ethyl acetate (1:1). The organic layer was dried over anhydrous magnesium sulfate, and the solvent was dried in a vacuum distillation apparatus. After drying, it was recrystallized in an ethanol solvent (420 mL) to obtain 43 g of compound 12-3 (yield 81%).

Preparation of Compound 12

The compound 12-3 (43 g, 75 mmol) and 3 wt % (based on the weight of compound 12-3) of Pd/C catalyst were stirred in an ethanol solvent (390 mL), and then, 80% hydrazine solution (36 mL) was slowly added dropwise to the stirred solution at room temperature and heated and stirred at 100° C. for 12 hours. After stirring, tetrahydrofuran solvent (400 mL) was added to the reactant, and the mixture was filtered over Celite to remove the catalyst. The solvent in the filtrate was dried in a vacuum distillation apparatus. After drying, it was recrystallized in an ethanol solvent (300 mL) to obtain 29 g of compound 12 (yield 77%).

HR LC/MS/MS m/z calcd for $C_{30}H_{30}N_4O_2S$ (M+): 510.2089; found: 510.2093

SYNTHESIS EXAMPLE 13

Preparation of Compound 13

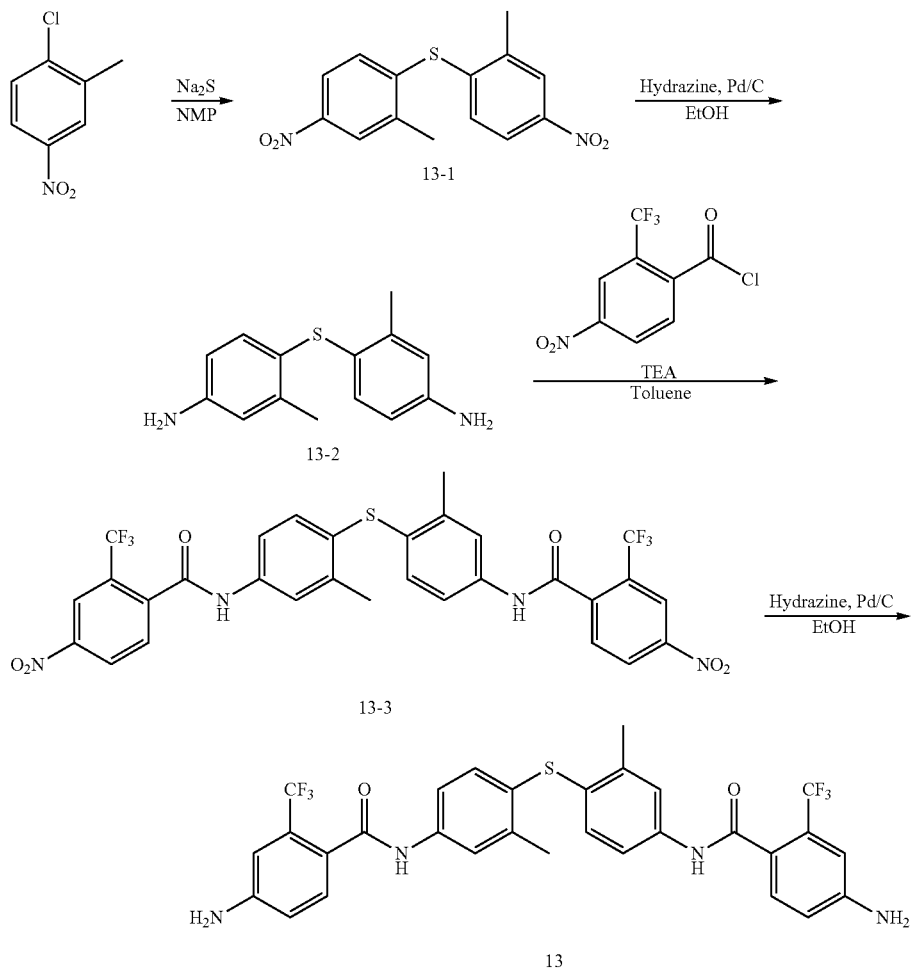

Preparation of Compound 13-1

2-Chloro-5-nitrotoluene (50 g, 292 mmol) and sodium sulfide ($Na_2S$) (11 g, 146 mmol) were heated and stirred for 8 hours at 200° C. in N-methyl-2-pyrrolidone (NMP) solvent (370 mL). After stirring, the reaction was cooled to room temperature, water (740 mL) was poured, and the resulting solid was filtered. The filtered solid was dissolved in ethyl acetate (500 mL) and extracted with water (500 mL). The organic layer was dried over anhydrous magnesium sulfate, and the solvent was dried in a vacuum distillation apparatus. After drying, it was recrystallized in an ethanol solvent (330 mL) to obtain 36 g of compound 13-1 (yield 81%).

Preparation of Compound 13-2

The compound 13-1 (36 g, 118 mmol) and 3 wt % (based on the weight of compound 13-1) of Pd/C catalyst were stirred in an ethanol solvent (350 mL), and then, 80% hydrazine solution (57 mL) was slowly added dropwise to the stirred solution at room temperature and heated and stirred at 100° C. for 12 hours. After stirring, tetrahydrofuran solvent (400 mL) was added to the reactant, and the mixture was filtered over Celite to remove the catalyst. The solvent in the filtrate was dried in a vacuum distillation apparatus. After drying, it was recrystallized in an ethanol solvent (220 mL) to obtain 19 g of compound 13-2 (yield 68%).

Preparation of Compound 13-3

The compound 13-2 (19 g, 77 mmol) and 4-nitro-2-(trifluoromethyl)benzoyl chloride (41 g, 163 mmol) were stirred in a toluene solvent (380 mL) while triethylamine (TEA) (31 g, 311 mmol) was added dropwise to the reactant at room temperature. The mixture was heated and stirred at 120° C. for 20 hours. After stirring, the reaction was cooled to room temperature and extracted with water and ethyl acetate (1:1). The organic layer was dried over anhydrous magnesium sulfate, and the solvent was dried in a vacuum distillation apparatus. After drying, it was recrystallized in an ethanol solvent (400 mL) to obtain 43 g of compound 13-3 (yield 83%).

Preparation of Compound 13

The compound 13-3 (43 g, 63 mmol) and 3 wt % (based on the weight of compound 13-3) of Pd/C catalyst were stirred in an ethanol solvent (400 mL), and then, 80% hydrazine solution (30 mL) was slowly added dropwise to the stirred solution at room temperature and heated and stirred at 100° C. for 12 hours. After stirring, tetrahydrofuran solvent (400 mL) was added to the reactant, and the mixture was filtered over Celite to remove the catalyst. The solvent in the filtrate was dried in a vacuum distillation apparatus. After drying, it was recrystallized in an ethanol solvent (300 mL) to obtain 31 g of compound 13 (yield 81%).

HR LC/MS/MS m/z calcd for $C_{30}H_{24}F_6N_4O_2S$ (M+): 618.1524; found: 618.1521

SYNTHESIS EXAMPLE 14

Preparation of Compound 14

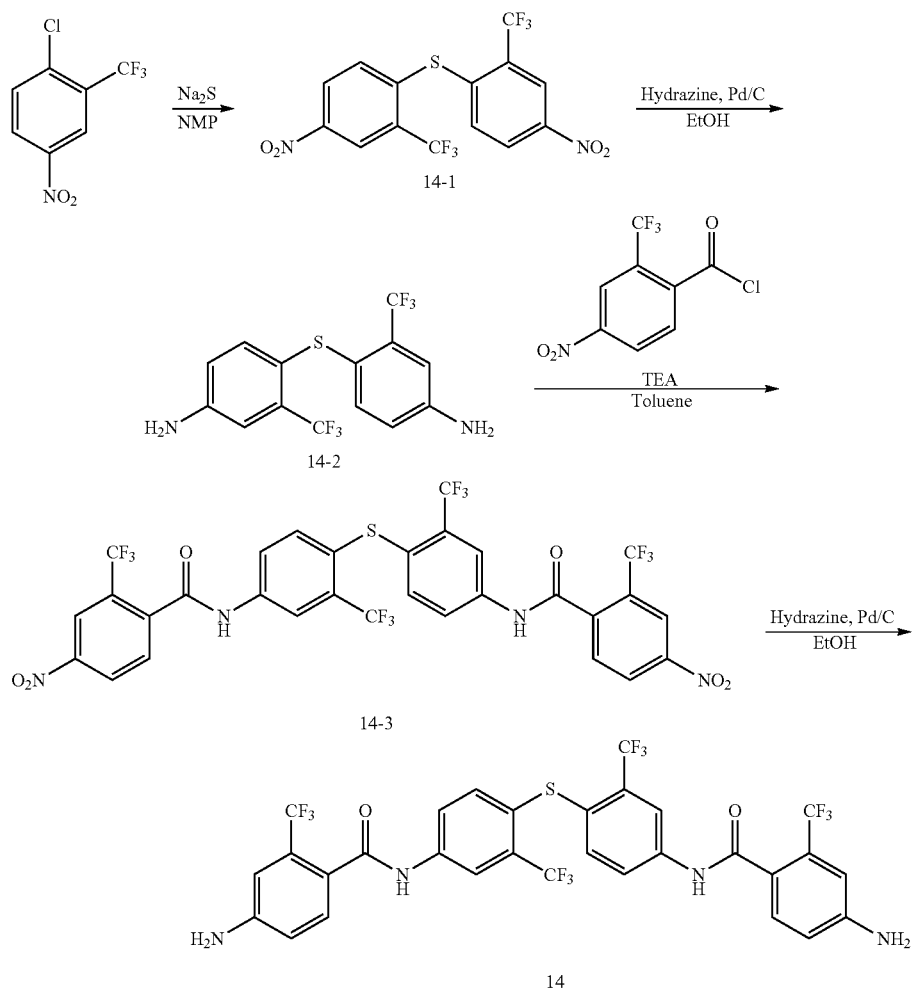

Preparation of Compound 14-1

2-Chloro-5-nitrobenzotrifluoride (50 g, 222 mmol) and sodium sulfide ($Na_2S$) (8 g, 111 mmol) were heated and stirred for 8 hours at 200° C. in N-methyl-2-pyrrolidone (NMP) solvent (460 mL). After stirring, the reaction was cooled to room temperature, water (920 mL) was poured, and the resulting solid was filtered. The filtered solid was dissolved in ethyl acetate (500 mL) and extracted with water (500 mL). The organic layer was dried over anhydrous magnesium sulfate, and the solvent was dried in a vacuum distillation apparatus. After drying, it was recrystallized in an ethanol solvent (380 mL) to obtain 37 g of compound 14-1 (yield 83%).

Preparation of Compound 14-2

The compound 14-1 (37 g, 89 mmol) and 3 wt % (based on the weight of compound 14-1) of Pd/C catalyst were stirred in an ethanol solvent (400 mL), and then, 80% hydrazine solution (43 mL) was slowly added dropwise to the stirred solution at room temperature and heated and stirred at 100° C. for 12 hours. After stirring, tetrahydrofuran solvent (400 mL) was added to the reactant, and the mixture was filtered over Celite to remove the catalyst. The solvent in the filtrate was dried in a vacuum distillation apparatus. After drying, it was recrystallized in an ethanol solvent (220 mL) to obtain 21 g of compound 14-2 (yield 69%).

Preparation of Compound 14-3

The compound 14-2 (21 g, 59 mmol) and 4-nitro-2-(trifluoromethyl)benzoyl chloride (31 g, 125 mmol) were stirred in a toluene solvent (300 mL) while triethylamine (TEA) (24 g, 238 mmol) was added dropwise to the reactant at room temperature. The mixture was heated and stirred at 120° C. for 20 hours. After stirring, the reaction was cooled to room temperature and extracted with water and ethyl acetate (1:1). The organic layer was dried over anhydrous magnesium sulfate, and the solvent was dried in a vacuum distillation apparatus. After drying, it was recrystallized in an ethanol solvent (350 mL) to obtain 38 g of compound 14-3 (yield 83%).

Preparation of Compound 14

The compound 14-3 (38 g, 48 mmol) and 3 wt % (based on the weight of compound 14-3) of Pd/C catalyst were stirred in an ethanol solvent (400 mL), and then, 80% hydrazine solution (23 mL) was slowly added dropwise to the stirred solution at room temperature and heated and stirred at 100° C. for 12 hours. After stirring, tetrahydrofuran solvent (350 mL) was added to the reactant, and the mixture was filtered over Celite to remove the catalyst. The solvent in the filtrate was dried in a vacuum distillation apparatus. After drying, it was recrystallized in an ethanol solvent (260 mL) to obtain 28 g of compound 14 (yield 82%).

HR LC/MS/MS m/z calcd for $C_{30}H_{18}F_{12}N_4O_2S$ (M+): 726.0959; found: 726.0960

SYNTHESIS EXAMPLE 15

Preparation of Compound 15

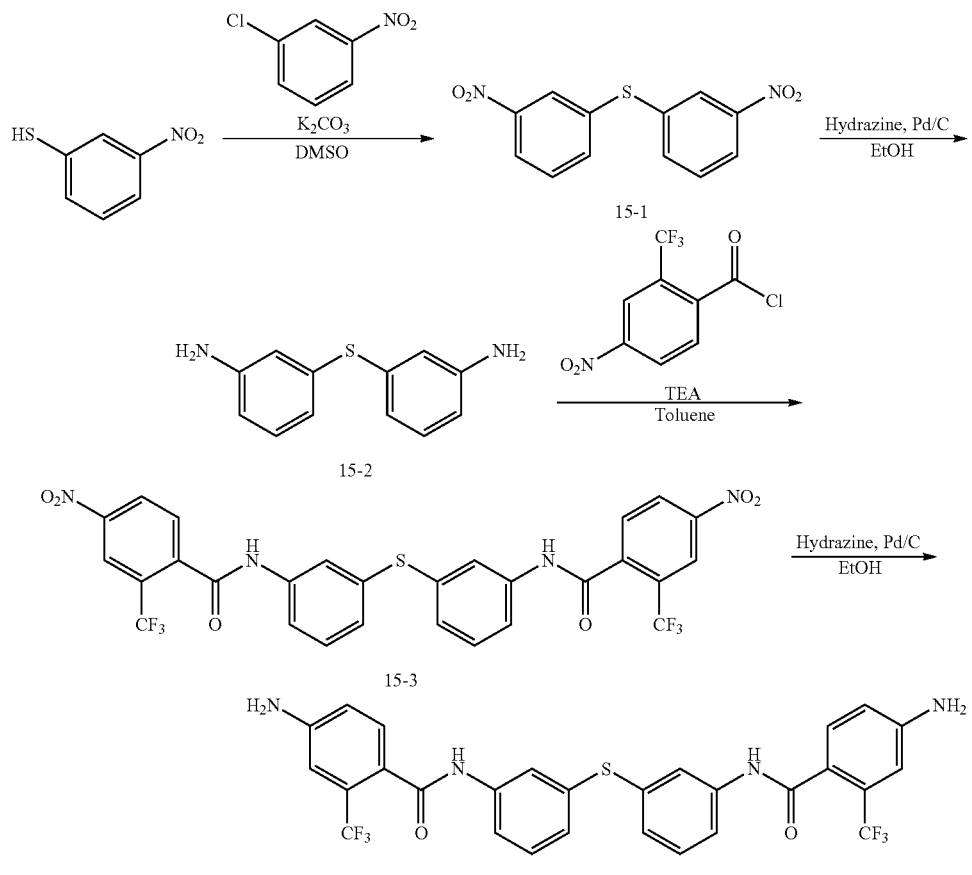

Preparation of Compound 15-1

3-nitrobenzenethiol (25 g, 161 mmol), 1-choloro-3-nitrobenzene (25 g, 161 mmol) and potassium carbonate (26 g) were heated and stirred for 6 hours at 190° C. in dimethylsulfoxide (DMSO) solvent (300 mL). After stirring, the reaction was cooled to room temperature, water (600 mL) was poured, and the resulting solid was filtered. The filtered solid was dissolved in ethyl acetate (500 mL) and extracted with water (500 mL). The organic layer was dried over anhydrous magnesium sulfate, and the solvent was dried in a vacuum distillation apparatus. After drying, it was recrystallized in an ethanol solvent (380 mL) to obtain 40 g of compound 15-1 (yield 90%).

Preparation of Compound 15-2

The compound 15-1 (40 g, 144 mmol) and 3 wt % (based on the weight of compound 15-1) of Pd/C catalyst were stirred in an ethanol solvent (300 mL), and then, 80% hydrazine solution (70 mL) was slowly added dropwise to the stirred solution at room temperature and heated and stirred at 100° C. for 12 hours. After stirring, tetrahydrofuran solvent (400 mL) was added to the reactant, and the mixture was filtered over Celite to remove the catalyst. The solvent in the filtrate was dried in a vacuum distillation apparatus. After drying, it was recrystallized in an ethanol solvent (200 mL) to obtain 20 g of compound 15-2 (yield 66%).

Preparation of Compound 15-3

The compound 15-2 (20 g, 95 mmol) and 4-nitro-2-(trifluoromethyl)benzoyl chloride (49 g, 194 mmol) were stirred in a toluene solvent (450 mL) while triethylamine (TEA) (37 g, 370 mmol) was added dropwise to the reactant at room temperature. The mixture was heated and stirred at 120° C. for 20 hours. After stirring, the reaction was cooled to room temperature and extracted with water and ethyl acetate (1:1). The organic layer was dried over anhydrous magnesium sulfate, and the solvent was dried in a vacuum distillation apparatus. After drying, it was recrystallized in an ethanol solvent (460 mL) to obtain 47 g of compound 15-3 (yield 79%).

Preparation of Compound 15

The compound 15-3 (47 g, 72 mmol) and 3 wt % (based on the weight of compound 15-3) of Pd/C catalyst were stirred in an ethanol solvent (440 mL), and then, 80% hydrazine solution (35 mL) was slowly added dropwise to the stirred solution at room temperature and heated and stirred at 100° C. for 12 hours. After stirring, tetrahydrofuran solvent (400 mL) was added to the reactant, and the mixture was filtered over Celite to remove the catalyst. The solvent in the filtrate was dried in a vacuum distillation apparatus. After drying, it was recrystallized in an ethanol solvent (300 mL) to obtain 31 g of compound 15 (yield 75%).

HR LC/MS/MS m/z calcd for $C_{28}H_{20}F_6N_4O_2S$ (M+): 590.1211; found: 590.1212

SYNTHESIS EXAMPLE 16

Preparation of Compound 16

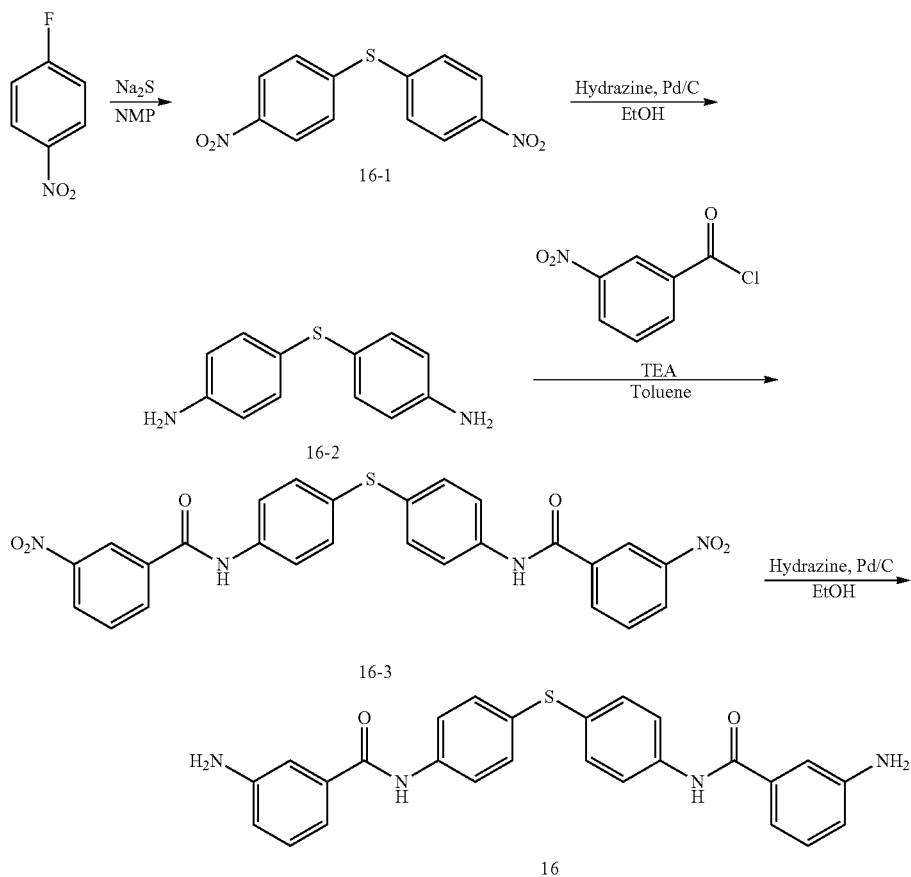

Preparation of Compound 16-1

4-Fluoronitrobenzene (50 g, 354 mmol) and sodium sulfide ($Na_2S$) (13 g, 177 mmol) were heated and stirred for 8 hours at 200° C. in N-methyl-2-pyrrolidone (NMP) solvent (400 mL). After stirring, the reaction was cooled to room temperature, water (800 mL) was poured, and the resulting solid was filtered. The filtered solid was dissolved in ethyl acetate (500 mL) and extracted with water (500 mL). The organic layer was dried over anhydrous magnesium sulfate, and the solvent was dried in a vacuum distillation apparatus. After drying, it was recrystallized in an ethanol solvent (380 mL) to obtain 41 g of compound 16-1 (yield 85%).

Preparation of Compound 16-2

The compound 16-1 (41 g, 148 mmol) and 3 wt % (based on the weight of compound 16-1) of Pd/C catalyst were stirred in an ethanol solvent (390 mL), and then, 80% hydrazine solution (72 mL) was slowly added dropwise to the stirred solution at room temperature and heated and stirred at 100° C. for 12 hours. After stirring, tetrahydrofuran solvent (400 mL) was added to the reactant, and the mixture was filtered over Celite to remove the catalyst. The solvent in the filtrate was dried in a vacuum distillation apparatus. After drying, it was recrystallized in an ethanol solvent (200 mL) to obtain 20 g of compound 16-2 (yield 65%).

Preparation of Compound 16-3

The compound 16-2 (20 g, 95 mmol) and 3-nitrobenzoyl chloride (35 g, 194 mmol) were stirred in a toluene solvent (360 mL) while triethylamine (TEA) (37 g, 370 mmol) was added dropwise to the reactant at room temperature. The mixture was heated and stirred at 120° C. for 20 hours. After stirring, the reaction was cooled to room temperature and extracted with water and ethyl acetate (1:1). The organic layer was dried over anhydrous magnesium sulfate, and the solvent was dried in a vacuum distillation apparatus. After drying, it was recrystallized in an ethanol solvent (300 mL) to obtain 36 g of compound 16-3 (yield 76%).

Preparation of Compound 16

The compound 16-3 (36 g, 70 mmol) and 3 wt % (based on the weight of compound 16-3) of Pd/C catalyst were stirred in an ethanol solvent (400 mL), and then, 80% hydrazine solution (34 mL) was slowly added dropwise to the stirred solution at room temperature and heated and stirred at 100° C. for 12 hours. After stirring, tetrahydrofuran solvent (400 mL) was added to the reactant, and the mixture was filtered over Celite to remove the catalyst. The solvent in the filtrate was dried in a vacuum distillation apparatus. After drying, it was recrystallized in an ethanol solvent (200 mL) to obtain 22 g of compound 16 (yield 72%).

HR LC/MS/MS m/z calcd for $C_{26}H_{22}N_4O_2S$ (M+): 454.1463; found: 454.1460

EXAMPLE 1

An organic solvent, DEAc (N,N-diethylacetamide) (225 mL) was charged into a reactor in a nitrogen stream, and then 45 g (0.055 mol) of the diamine compound 1 prepared in Synthesis Example 1 was added to dissolve it while maintaining the reactor temperature at 25° C. To the solution with the compound 1 added, 16 g (0.055 mol) of BPDA (biphenyl-tetracarboxylic acid dianhydride) as an acid anhydride was added at the same temperature and stirred for 24 hours to obtain a polyimide precursor composition.

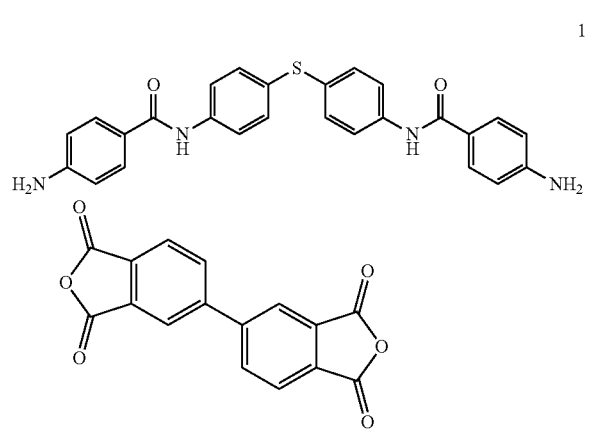

1

BPDA

EXAMPLE 2

An organic solvent, DEAc (130 mL) was charged into a reactor in a nitrogen stream, and then 26 g (0.054 mol) of the diamine compound 2 prepared in Synthesis Example 2 was added to dissolve it while maintaining the reactor temperature at 25° C. To the solution with the compound 2 added, 15 g (0.054 mol) of BPDA as an acid anhydride was added at the same temperature and stirred for 24 hours to obtain a polyimide precursor composition.

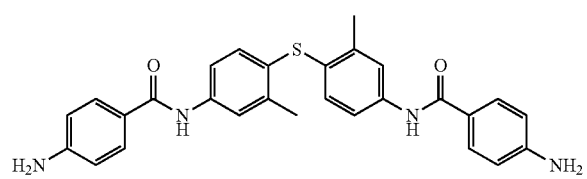

2

EXAMPLE 3

An organic solvent, DEAc (150 mL) was charged into a reactor in a nitrogen stream, and then 27 g (0.046 mol) of the diamine compound 3 prepared in Synthesis Example 3 was added to dissolve it while maintaining the reactor temperature at 25° C. To the solution with the compound 3 added, 13 g (0.046 mol) of BPDA as an acid anhydride was added at the same temperature and stirred for 24 hours to obtain a polyimide precursor composition.

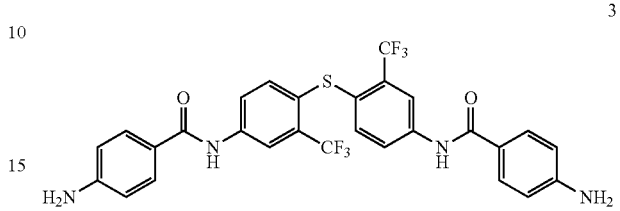

3

EXAMPLE 4

An organic solvent, DEAc (140 mL) was charged into a reactor in a nitrogen stream, and then 28 g (0.047 mol) of the diamine compound 8 prepared in Synthesis Example 8 was added to dissolve it while maintaining the reactor temperature at 25° C. To the solution with the compound 8 added, 13 g (0.047 mol) of BPDA as an acid anhydride was added at the same temperature and stirred for 24 hours to obtain a polyimide precursor composition.

EXAMPLE 5

An organic solvent, DEAc (100 mL) was charged into a reactor in a nitrogen stream, and then 20 g (0.038 mol) of the diamine compound 10 prepared in Synthesis Example 10 was added to dissolve it while maintaining the reactor temperature at 25° C. To the solution with the compound 10 added, 11 g (0.038 mol) of BPDA as an acid anhydride was added at the same temperature and stirred for 24 hours to obtain a polyimide precursor composition.

EXAMPLE 6

An organic solvent, DEAc (140 mL) was charged into a reactor in a nitrogen stream, and then 28 g (0.038 mol) of the diamine compound 14 prepared in Synthesis Example 14 was added to dissolve it while maintaining the reactor temperature at 25° C. To the solution with the compound 14 added, 11 g (0.038 mol) of BPDA as an acid anhydride was added at the same temperature and stirred for 24 hours to obtain a polyimide precursor composition.

EXAMPLE 7

An organic solvent, DEAc (130 mL) was charged into a reactor in a nitrogen stream, and then 26 g (0.053 mol) of the diamine compound 2 prepared in Synthesis Example 2 was added to dissolve it while maintaining the reactor temperature at 25° C. To the solution with the compound 2 added, 11 g (0.053 mol) of pyromellitic dianhydride (PMDA) as an acid anhydride was added at the same temperature and stirred for 24 hours to obtain a polyimide precursor composition.

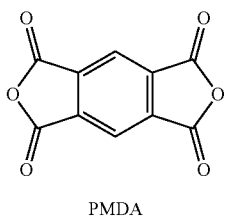

PMDA

EXAMPLE 8

An organic solvent, DEAc (140 mL) was charged into a reactor in a nitrogen stream, and then 28 g (0.047 mol) of the diamine compound 8 prepared in Synthesis Example 8 was added to dissolve it while maintaining the reactor temperature at 25° C. To the solution with the compound 8 added, 10 g (0.047 mol) of PMDA as an acid anhydride was added at the same temperature and stirred for 24 hours to obtain a polyimide precursor composition.

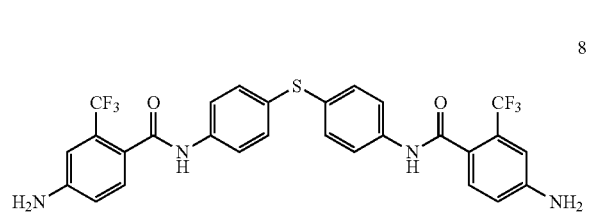

8

EXAMPLE 9

An organic solvent, DEAc (100 mL) was charged into a reactor in a nitrogen stream, and then 20 g (0.034 mol) of the diamine compound 10 prepared in Synthesis Example 10 was added to dissolve it while maintaining the reactor temperature at 25° C. To the solution with the compound 10 added, 7 g (0.034 mol) of PMDA as an acid anhydride was added at the same temperature and stirred for 24 hours to obtain a polyimide precursor composition.

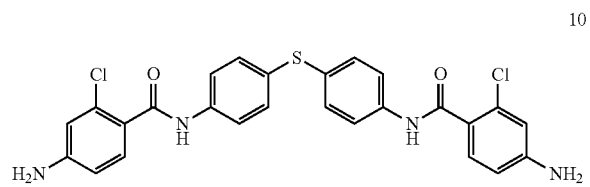 [SMILES: Nc1ccc(C(=O)Nc2ccc(Sc3ccc(NC(=O)c4ccc(N)cc4Cl)cc3)cc2)c(Cl)c1]

10

COMPARATIVE EXAMPLE 1

An organic solvent, DEAc (30 mL) was charged into a reactor in a nitrogen stream, and then 6 g (0.063 mol) of p-phenylenediamine (PDA) as a diamine compound was added to dissolve it while maintaining the reactor temperature at 25° C. To the solution with PDA added, 18 g (0.063 mol) of BPDA as an acid anhydride was added at the same temperature and stirred for 24 hours to obtain a polyimide precursor composition.

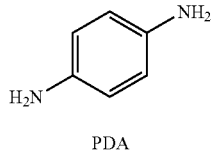

PDA

COMPARATIVE EXAMPLE 2

An organic solvent, DEAc (110 mL) was charged into a reactor in a nitrogen stream, and then 22 g (0.071 mol) of 2,2'-bis(trifluoromethyl)benzidine (TFMB) as a diamine compound was added to dissolve it while maintaining the reactor temperature at 25° C. To the solution with TFMB added, 15 g (0.071 mol) of PMDA as an acid anhydride was added at the same temperature and stirred for 24 hours to obtain a polyimide precursor composition.

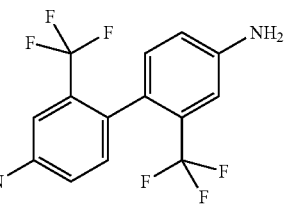

TFMB

COMPARATIVE EXAMPLE 3

A polyimide precursor composition was obtained according to the same process as in Example 1, except that the following control compound C, in which the phenyl ring substituted with —NH—(C=O)— was not boned to both ends of the molecule, was used instead of the diamine compound 1.

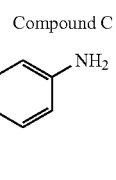

Compound C

EXPERIMENTAL EXAMPLE 1

Each of the polyimide precursor compositions (solutions) prepared in Examples 1 to 9 and Comparative Examples 1 to 3 was spin coated on a glass substrate. The glass substrate coated with each polyimide precursor solution was placed in an oven, heated at a rate of 5° C./min and cured at 80° C. for 30 minutes and at 300° C. for 30 minutes to prepare each polyimide film.

<Evaluation of Properties of Polyimide Film>
1. Yellowness Index (YI)

Yellowness index (YI) was measured with Color Eye 7000A.

2. Transmittance

Transmittance at a wavelength of 550 nm was measured with the transmittance meter (model name HR-100, a Murakami Color Research Laboratory) based on JIS K7105.

3. Refractive Index

For each polyimide film prepared in Experimental Example 1, a refractive index at a wavelength of 532 nm was measured using a prism coupler.

4. Glass Transition Temperature (Tg)

Each polyimide film obtained in Experimental Example 1 was cut to 5×20 mm to prepare a specimen, and then the specimen was loaded using an accessory of TMA (thermo-mechanical analyzer) (Q400, TA Instruments). The first temperature-rising step was carried out at a heating rate of 5° C./min from 100 to 350° C. and then the cooling step was carried out at a cooling rate of 4° C./min from 350 to 100° C. The inflection point shown in the temperature-rising section during the second temperature-rising step was defined as Tg.

The yellowness index, transmittance, refractive index, and Tg values of the polyimide film are shown in Table 1 below.

TABLE 1

| | Thickness of polyimide film (μm) | Yellowness index (YI) | Transmittance at 550 nm | Refractive index at 532 nm | | Tg (° C.) |
| --- | --- | --- | --- | --- | --- | --- |
| | | | | In plane | thickness | |
| Example 1 | 8.90 | 12.26 | 87.1 | 1.7965 | 1.6926 | 320 |
| Example 2 | 8.84 | 7.14 | 85.2 | 1.7691 | 1.6533 | 308 |
| Example 3 | 8.87 | 6.08 | 86.5 | 1.7789 | 1.6885 | 313 |
| Example 4 | 8.95 | 5.59 | 86.9 | 1.7892 | 1.6899 | 316 |
| Example 5 | 8.81 | 10.98 | 87.8 | 1.8064 | 1.7053 | 319 |
| Example 6 | 8.80 | 5.03 | 87.4 | 1.7681 | 1.6497 | 310 |
| Example 7 | 10.20 | 9.11 | 87.5 | 1.6911 | 1.5288 | 325 |
| Example 8 | 9.77 | 6.65 | 88.0 | 1.7188 | 1.5421 | 329 |
| Example 9 | 10.53 | 10.70 | 88.9 | 1.7706 | 1.5741 | 328 |
| Comparative Example 1 | 8.89 | 23.36 | 84.8 | 1.7674 | 1.6308 | 307 |
| Comparative Example 2 | 11.01 | 12.12 | 86.9 | 1.6649 | 1.5117 | 324 |
| Comparative Example 3 | 8.74 | 15.16 | 86.5 | 1.7206 | 1.6772 | 319 |

As can be seen from Table 1, it is found that the polyimide films (Examples 1 to 9) prepared by using the polyimide precursor composition comprising the novel diamine compound according to the present invention have overall excellent light transmittance and yellowness index and improved refractive index, compared to the polyimide films of Comparative Examples 1 to 3 prepared by using the polyimide precursor composition comprising the same acid anhydride but a diamine compound having a different structure from the diamine compound of the present invention.

While the present invention has been particularly shown and described with reference to specific embodiments thereof, it will be apparent to those skilled in the art that this specific description is merely a preferred embodiment and that the scope of the invention is not limited thereby. It is therefore intended that the scope of the invention be defined by the claims appended hereto and their equivalents.

What is claimed is:

1. A diamine compound of the following formula 1:

[Formula 1]

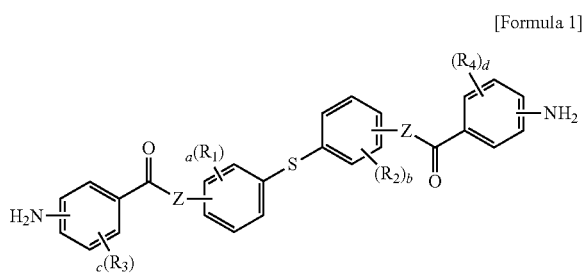

In the formula 1,

Z is —NH—, $R_1$ to $R_4$ are each independently hydrogen, deuterium, a halogen atom, a cyano group, a substituted or unsubstituted alkyl group having 1 to 30 carbon atoms, a substituted or unsubstituted haloalkyl group having 1 to 30 carbon atoms, a substituted or unsubstituted alkylsilyl group having 1 to 30 carbon atoms, a substituted or unsubstituted arylsilyl group having 6 to 30 carbon atoms, a substituted or unsubstituted alkylamino group having 1 to 30 carbon atoms, a substituted or unsubstituted arylamino group having 6 to 30 carbon atoms, a substituted or unsubstituted alkoxy group having 1 to 30 carbon atoms, a substituted or unsubstituted alkylthio group having 1 to 30 carbon atoms, a substituted or unsubstituted arylthiol group having 6 to 30 carbon atoms, a substituted or unsubstituted aryl group having 6 to 30 carbon atoms, a substituted or unsubstituted aralkyl group having 6 to 30 carbon atoms, a substituted or unsubstituted aryloxy group having 6 to 30 carbon atoms, a substituted or unsubstituted cycloalkyl group having 3 to 30 carbon atoms, an amide group, a substituted or unsubstituted cycloalkyloxy group having 3 to 30 carbon atoms, a substituted or unsubstituted cycloalkylthio group having 1 to 30 carbon atoms, an ester group, an azide group, or a substituted or unsubstituted (3-30 membered) heteroaryl group comprising at least one selected from B, N, O, S, P (═O), Si and P, a, b, c and d are each an integer of 0 to 4, and when a, b, c and d are each an integer of 2 to 4, each of a, b, c and d is the same or different, and each of the two amino group substituents is substituted at a meta-position or para-position of each of the benzene rings with respect to the carbonyl group in each of the benzene rings.

2. The diamine compound according to claim 1, wherein $R_1$ to $R_4$ are each independently hydrogen, a halogen atom, a cyano group, or an alkyl group having 1 to 6 carbon atoms which is unsubstituted or substituted with at least one halogen atom, and a, b, c and d are each an integer of 0 to 2.

3. The diamine compound according to claim 1, wherein $R_1$ to $R_4$ are each independently hydrogen, methyl, trifluoromethyl, F, Cl or a cyano group, and a, b, c and d are each an integer of 0 to 2.

4. The diamine compound according to claim 1, wherein the diamine compound of the formula 1 is selected from compounds of the following structural formulae 1 to 16:

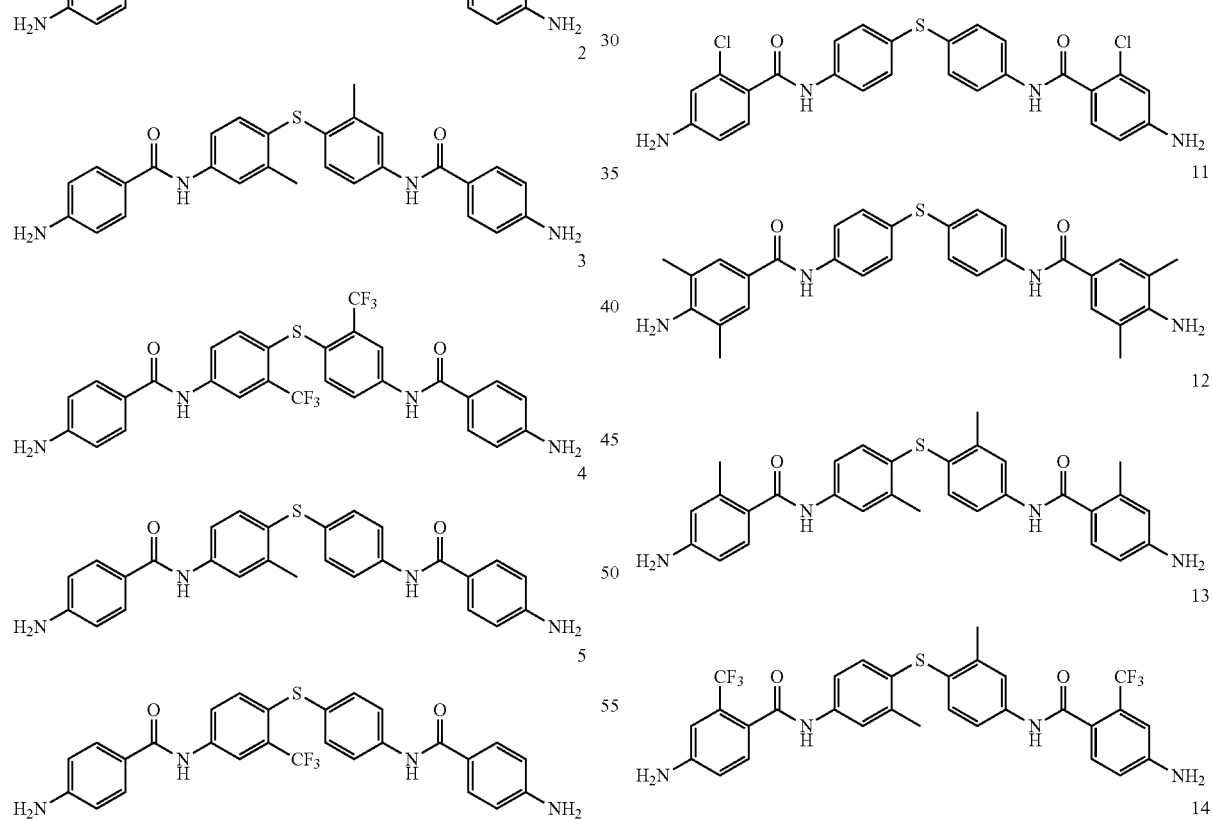

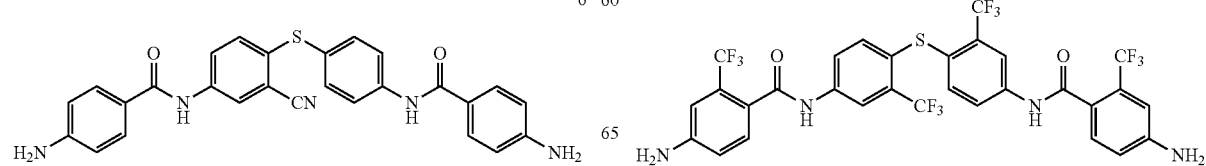

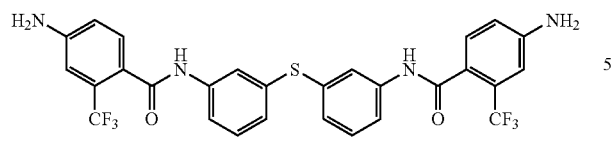
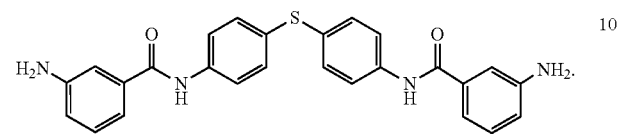
* * * * *